(12) United States Patent
Prager

(10) Patent No.: US 11,179,519 B2
(45) Date of Patent: Nov. 23, 2021

(54) INJECTION DEVICE AND A SUPPLEMENTAL DEVICE CONFIGURED FOR ATTACHMENT THERETO

(71) Applicant: Sanofi-Aventis Deutschland GMBH, Frankfurt am Main (DE)

(72) Inventor: Roman Prager, Gänserndorf (AT)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 64 days.

(21) Appl. No.: 16/531,384

(22) Filed: Aug. 5, 2019

(65) Prior Publication Data
US 2019/0351142 A1    Nov. 21, 2019

Related U.S. Application Data

(62) Division of application No. 15/503,979, filed as application No. PCT/EP2015/068323 on Aug. 10, 2015, now Pat. No. 10,806,860.

(30) Foreign Application Priority Data

Aug. 15, 2014   (EP) ..................................... 14181118

(51) Int. Cl.
  *A61M 5/24* (2006.01)
  *A61M 5/315* (2006.01)
  *A61M 5/31* (2006.01)

(52) U.S. Cl.
  CPC .......... *A61M 5/24* (2013.01); *A61M 5/31528* (2013.01); *A61M 2005/3125* (2013.01);
  (Continued)

(58) Field of Classification Search
  CPC ................ A61M 5/31528; A61M 5/24; A61M 2005/3125; A61M 2005/3126; A61M 2205/3306; A61M 2205/3561
  See application file for complete search history.

(56) References Cited

U.S. PATENT DOCUMENTS 3,709,524 A * 1/1973 McKee .................. G07C 9/253
                                                462/55
5,469,294 A   11/1995 Wilt et al.
(Continued)

FOREIGN PATENT DOCUMENTS

| CN | 1399528 | 2/2003 |
| CN | 102846308 | 1/2013 |

(Continued)

OTHER PUBLICATIONS

International Search Report and Written Opinion in International Application No. PCT/EP2015/068323, dated Mar. 7, 2016, 14 pages.

(Continued)

*Primary Examiner* — Nathan R Price
*Assistant Examiner* — Tasnim Mehjabin Ahmed
(74) *Attorney, Agent, or Firm* — Fish & Richardson P.C.

(57) ABSTRACT

A supplemental device configured for attachment to an injection device, the supplemental device comprising: a camera configured to generate camera output indicative of a scene viewable by the camera, and to be located on an optical path with a surface of an injection device attached to the supplemental device in use; a light source having an emission spectrum and configured to illuminate the surface with light within the emission spectrum in use; and a filter configured to be located on the optical path between the camera and the surface in use, the filter being substantially opaque to light across the entire emission spectrum of the light source and substantially transparent to light of at least one frequency outside the emission spectrum of the light source.

20 Claims, 12 Drawing Sheets

(52) U.S. Cl.
CPC ............ *A61M 2005/3126* (2013.01); *A61M 2205/3306* (2013.01); *A61M 2205/3561* (2013.01); *A61M 2205/3592* (2013.01); *A61M 2205/502* (2013.01); *A61M 2205/52* (2013.01); *A61M 2205/581* (2013.01); *A61M 2205/6045* (2013.01); *A61M 2205/6063* (2013.01); *A61M 2205/6072* (2013.01); *A61M 2205/6081* (2013.01)

(56) References Cited

U.S. PATENT DOCUMENTS

| | | | | |
|---|---|---|---|---|
| 5,834,894 | A | * | 11/1998 | Shirasaki ............ H01L 51/5012 313/509 |
| 8,036,444 | B2 | | 10/2011 | Nielsen |
| 2001/0008513 | A1 | | 7/2001 | Arai |
| 2004/0232052 | A1 | * | 11/2004 | Call .................. B01D 21/2455 209/143 |
| 2004/0263643 | A1 | | 12/2004 | Imaizuni |
| 2006/0167419 | A1 | * | 7/2006 | Fiechter ............ A61M 5/31553 604/181 |
| 2006/0217594 | A1 | | 9/2006 | Ferguson |
| 2007/0228306 | A1 | | 10/2007 | Gannon et al. |
| 2008/0094623 | A1 | | 4/2008 | Schuurmans |
| 2009/0001164 | A1 | * | 1/2009 | Brock .................. G07D 7/0043 235/462.01 |
| 2013/0006178 | A1 | | 1/2013 | Pinho et al. |
| 2013/0274596 | A1 | | 10/2013 | Azizian et al. |
| 2014/0027333 | A1 | * | 1/2014 | Pawlowski ............ A61M 5/001 206/438 |
| 2014/0132945 | A1 | | 5/2014 | Sandford |
| 2014/0194826 | A1 | * | 7/2014 | Nielsen ............ A61M 5/31568 604/189 |
| 2015/0018776 | A1 | * | 1/2015 | Schenker .......... A61M 5/31563 604/207 |
| 2015/0148665 | A1 | * | 5/2015 | Sato ................. A61B 17/06166 600/424 |

FOREIGN PATENT DOCUMENTS

| | | |
|---|---|---|
| CN | 103648555 | 3/2014 |
| EP | 2 746 771 | 6/2014 |
| JP | 2005-013611 | 1/2005 |
| JP | 2006-187630 | 7/2006 |
| JP | 2010-537250 | 12/2010 |
| WO | WO 01/22870 | 4/2001 |
| WO | WO 2006/021903 | 3/2006 |
| WO | 2008-510982 | 4/2008 |
| WO | WO 2010/115762 | 10/2010 |
| WO | WO 2011/007212 | 1/2011 |
| WO | WO 2011/117212 | 9/2011 |
| WO | WO 2013/120776 | 8/2013 |
| WO | WO 2013/180127 | 12/2013 |
| WO | WO 2016/023846 | 2/2016 |

OTHER PUBLICATIONS

International Preliminary Report on Patentability in International Application No. PCT/EP2015/068323, dated Feb. 21, 2017, 9 pages.

* cited by examiner

INJECTION DEVICE AND A SUPPLEMENTAL DEVICE CONFIGURED FOR ATTACHMENT THERETO

CROSS-REFERENCE TO RELATED APPLICATIONS

This application is a divisional of U.S. patent application Ser. No. 15/503,979, filed Feb. 14, 2017, which is a U.S. national stage application under 35 USC § 371 of International Application No. PCT/EP2015/068323, filed on Aug. 10, 2015, which claims priority to European Patent Application No. 14181118.2 filed on Aug. 15, 2014, the entire contents of which are incorporated herein by reference.

TECHNICAL FIELD

The present disclosure relates to an injection device, such as an insulin injection device, and a supplemental device configured for attachment thereto.

BACKGROUND

A variety of diseases exist that require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day.

WO2011/117212 discloses a supplemental device that can be attached to an injection device and used to record the quantity of medicament that a patient is injected with. In the case of a Sanofi Solostar™ injection device for instance, the amount of insulin a patient is injected with can be determined by analysing information which appears in a window of the injection device (referred to as the dosage window). This information is provided on a sleeve within the injection device and comprises a series of numbers. In use the sleeve rotates and causes the number aligned with the dosage window to either increase or decrease in amount depending on whether a quantity of insulin is being dialled or injected respectively.

The supplemental device in WO2011/117212 has an optical character recognition (OCR) reader to determine what particular number is viewable at a given time and uses this information to both determine and record how much insulin a person is injected with.

In order for this analysis to take place the supplemental device covers the dosage window, thereby preventing ambient light becoming incident on the window. A light source may be provided to illuminate the sleeve portion aligned with the dosage window. This improves the readability, by the OCR reader, of numbers on the sleeve aligned with the dosage window.

Disadvantageously, some light may reflect from the dosage window directly towards the OCR reader. This obscures the analysis of light which reflects from the sleeve where the number being analysed at a given time is provided. This decreases the reliability with which a number aligned with the dosage window at a given time can be determined. In other words, glare from the dosage window decreases the reliability with which a dialled quantity of insulin, or an injected quantity of insulin, can be determined.

Aspects of the present disclosure have been conceived with the foregoing in mind.

SUMMARY

According to an aspect there is provided a supplemental device configured for attachment to an injection device, the supplemental device comprising: a camera configured to generate camera output indicative of a scene viewable by the camera, and to be located on an optical path with a surface of an injection device attached to the supplemental device in use; a light source having an emission spectrum and configured to illuminate the surface with light within the emission spectrum in use; and a filter configured to be located on the optical path between the camera and the surface in use, the filter being substantially opaque to light across the entire emission spectrum of the light source and substantially transparent to light of at least one frequency outside the emission spectrum of the light source.

This may increase the reliability of the camera output obtained in use by preventing light from the light source being reflected into contact with the camera and influencing its output.

The supplemental device may further comprise a protection window that is configured to be located on the optical path between the filter and the surface in use, the protection window being substantially transparent to light of at least one frequency in the emission spectrum of the light source and to light of the at least one frequency outside the emission spectrum of the light source. In this arrangement the filter may be coupled to the protection window.

This may protect elements of the supplemental device located behind the protection window from dirt and/or water ingress. Coupling the filter to the protection window may enable the supplemental device to have a more compact size. Also, coupling the filter to the protection window may make it easier to arrange these components relative to one another, thereby increasing the ease and speed of manufacture of the supplemental device.

Alternatively, the supplemental device may further comprising a protection window, wherein the filter is configured to be located on the optical path between the protection window and the surface in use, the protection window being substantially transparent to light of at least one frequency in the emission spectrum of the light source and to light of the at least one frequency outside the emission spectrum of the light source. In this arrangement the filter may be coupled to the protection window.

This may protect elements of the supplemental device located behind the protection window from dirt and/or water ingress. Coupling the filter to the protection window may reduce the overall size of the supplemental device. Also, coupling the filter to the protection window may make it easier to arrange these components relative to one another, thereby increasing the ease and speed of manufacture of the supplemental device.

Alternatively, the supplemental device may further comprise a protection window that is configured to be located on the optical path between the camera and the surface in use, wherein at least part of the protection window comprises the filter. In this arrangement part of the protection window may be substantially transparent to light of at least one frequency in the emission spectrum of the light source.

This may protect elements of the supplemental device located behind the protection window from dirt and/or water ingress. Forming the filter as part of the protection window may reduce the overall size of the supplemental device and increase the ease and speed of manufacture of the supplemental device because the step of fixing the filter and protection window relative to one another no longer needs to be performed.

In all of the foregoing arrangements the light source may be configured to emit one of ultra violet, infrared and visible radiation, and the filter may be substantially transparent to another one of ultra violet, infrared and visible radiation.

The light source may be configured to emit ultraviolet radiation and the filter may be configured to block ultraviolet radiation while being transparent to visible radiation.

According to another aspect there is provided an injection device comprising: a sleeve on which is formed one or more markings indicating a dose of medicament; and a window through which a part of the sleeve is visible, the device being configured to change the part of the sleeve that is visible through the window as a medicament dose is dispensed; wherein the one or more markings are formed of a fluorescent material.

The fluorescent material may be provided on the sleeve in the shape of information that indicates a dose of medicament.

The fluorescent material may be provided on the sleeve such that the fluorescent material outlines the shape of information that indicates a dose of medicament.

The fluorescent material may be configured such that when illuminated with one of ultra violet, infrared and visible radiation the fluorescent material emits through the window optical fluorescence that is another one of ultra violet, infrared and visible radiation.

The fluorescent material is configured such that when illuminated with ultra violet radiation the fluorescent material emits visible radiation through the window.

Embodiments of the present disclosure will now be described, by way of example only, with reference to the accompanying drawings.

BRIEF DESCRIPTION OF THE DRAWINGS

The figures show:

FIG. 1b shows a perspective view of some detail of the injection device of FIG. 1a;

FIG. 2a: a schematic illustration of a supplemental device to be releasably attached to the injection device of FIG. 1a;

FIG. 2b: a perspective view of a supplemental device to be releasably attached to the injection device of FIG. 1a;

FIG. 3: a schematic view of the supplemental device of either FIG. 2a or 2b in a state where it is attached to the injection device of FIG. 1a;

FIG. 6: a side view of the supplemental device of FIG. 2b attached to the injection device of FIG. 1a;

DETAILED DESCRIPTION

The following disclosure will be described in the context of an insulin injection device however this is not intended to be limiting and the teachings herein may equally well be deployed with injection devices that eject other medicaments, or with other types of medical devices.

Figure 1A:
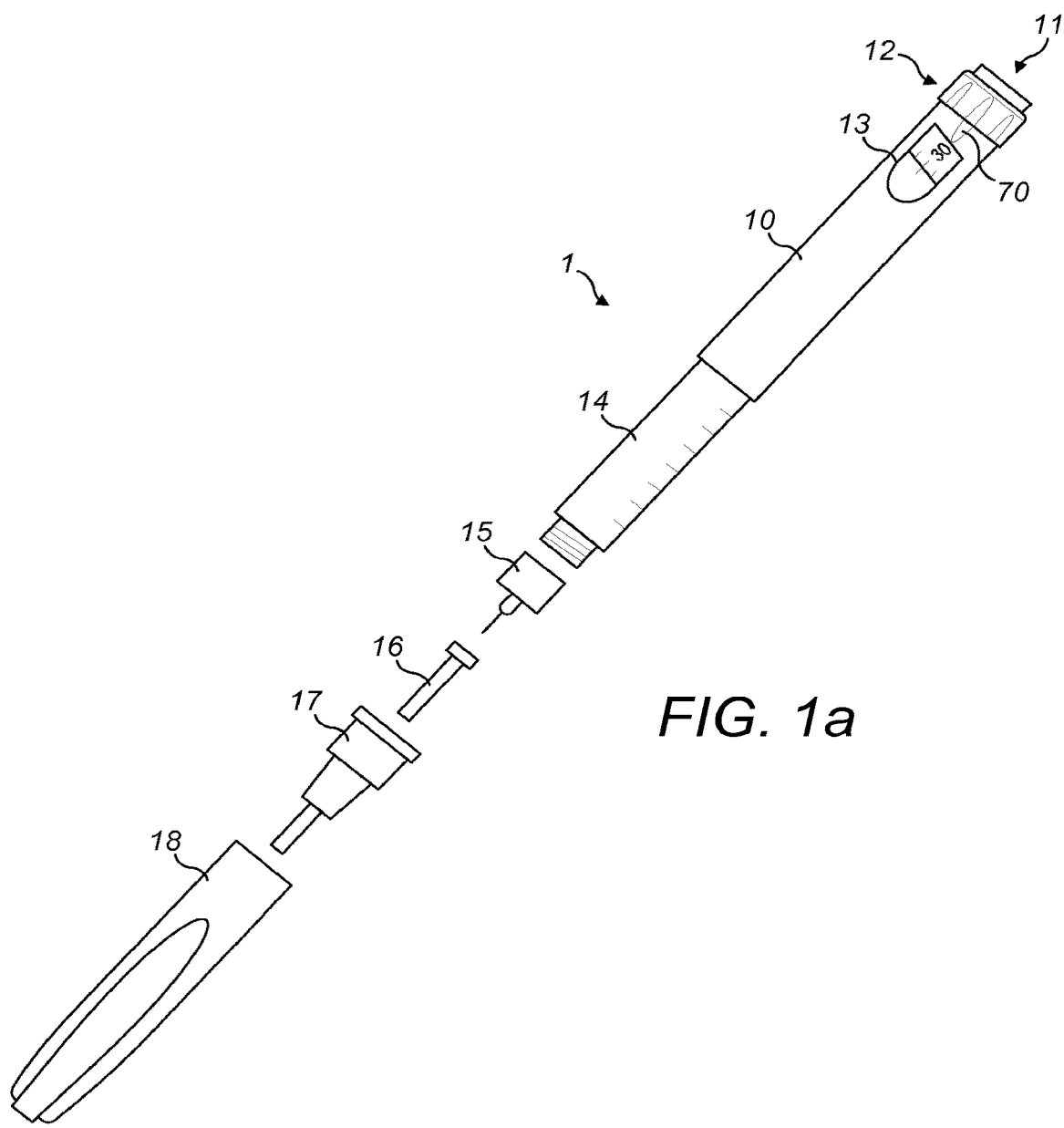
FIG. 1a: an exploded view of an injection device.

FIG. 1a is an exploded view of an injection device 1, which may for instance represent Sanofi's Solostar (R) insulin injection device.

The injection device 1 of FIG. 1a is a pre-filled, disposable injection device that comprises a housing 10 and contains an insulin container 14, to which a needle 15 can be affixed. The needle is protected by an inner needle cap 16 and an outer needle cap 17, which in turn can be covered by a cap 18. An insulin dose to be ejected from injection device 1 can be selected by turning the dosage knob 12, and the selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may for instance be 30 IUs, as shown in FIG. 1a.

It should be noted that the selected dose may equally well be displayed differently. A label (not shown) is provided on the housing 10. The label includes information about the medicament included within the injection device, including information identifying the medicament. The information identifying the medicament may be in the form of text, a colour, a barcode, QR code or the like.

Turning the dosage knob 12 causes a mechanical click sound to provide acoustical feedback to a user. The numbers displayed in dosage window 13 are printed on a sleeve that is contained in housing 10 and mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose is actually injected into the patient's body. Ejection of the insulin dose also causes a mechanical click sound, which is however different from the sounds produced when using dosage knob 12.

Before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards.

For simplicity of presentation, in the following, it will be exemplarily assumed that the ejected doses substantially correspond to the injected doses, so that, for instance when making a proposal for a dose to be injected next, this dose equals the dose that has to ejected by the injection device. Nevertheless, differences (e.g. losses) between the ejected doses and the injected doses may of course be taken into account.

Figure 1B:
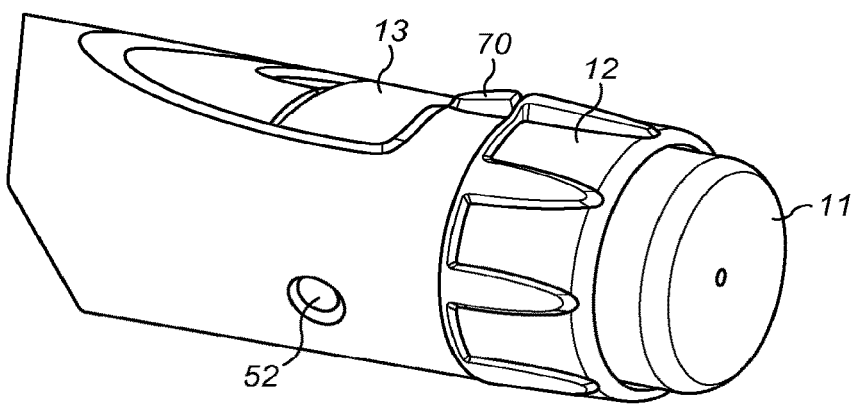

FIG. 1b is a close-up of the end of the injection device 1 and shows a locating rib 70 that is located between the viewing window 13 and the dosage knob 12.

Figure 2A:
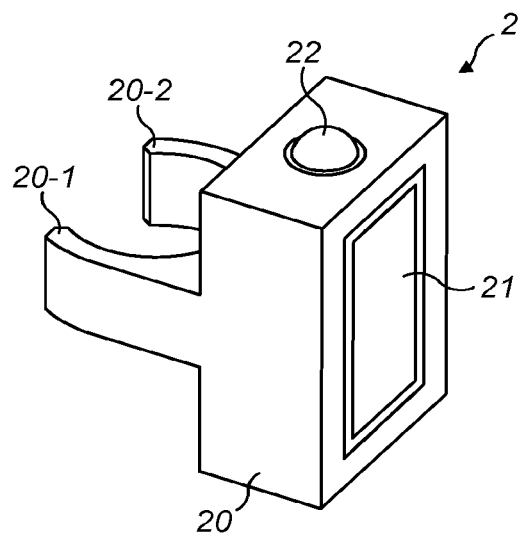

FIG. 2a is a schematic illustration of an embodiment of a supplemental device 2 to be releasably attached to injection device 1 of FIG. 1a. Supplemental device 2 comprises a housing 20 with a mating unit configured to embrace the housing 10 of injection device 1 of FIG. 1a, so that supplemental device 2 sits tightly on housing 10 of injection device 1, but is nevertheless removable from injection device 1, for instance when injection device 1 is empty and has to be replaced. FIG. 2a is highly schematic, and details of the physical arrangement are described below with reference to FIG. 2b.

Supplemental device 2 contains optical and acoustical sensors for gathering information from injection device 1. At least a part of this information e.g. a selected dose (and optionally a unit of this dose), is displayed via display unit 21 of supplemental device 2. The dosage window 13 of injection device 1 is obstructed by supplemental device 2 when attached to injection device 1.

Supplemental device 2 further comprises three user input transducers, illustrated schematically as a button 22. These input transducers 22 allow a user to turn on/off supplemental device 2, to trigger actions (e.g. to cause establishment of a connection to another device), or to confirm something.

Figure 2B:
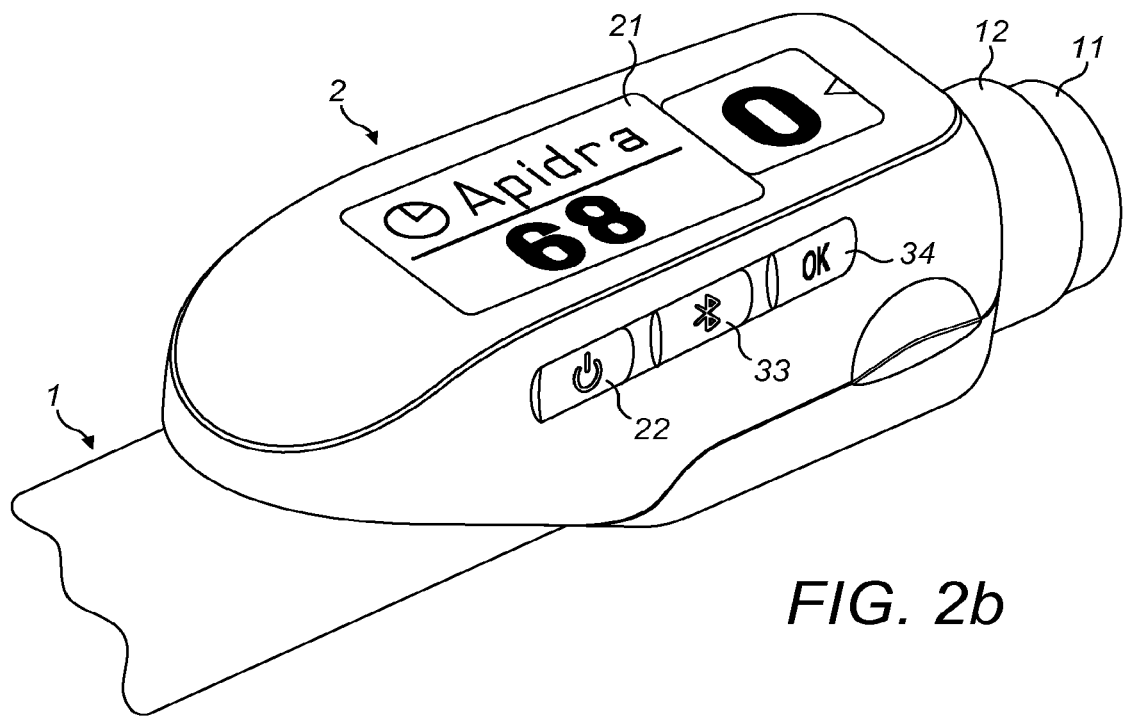

FIG. 2b is a schematic illustration of a second embodiment of a supplemental device 2 to be releasably attached to injection device 1 of FIG. 1a. Supplemental device 2 comprises a housing 20 with a mating unit configured to embrace the housing 10 of the injection device 1, so that supplemental device 2 sits tightly on housing 10, but is nevertheless removable from injection device 1.

Information is displayed via display unit 21 of supplemental device 2. The dosage window 13 of injection device 1 is obstructed by supplemental device 2 when attached to injection device 1. Supplemental device 2 further comprises three user input buttons or switches. A first button 22 is a power on/off button, via which the supplemental device 2 may be turned on and off. A second button 33 is a communications button. A third button 34 is a confirm or OK button. The buttons may be any suitable form of mechanical switch.

Figure 3:
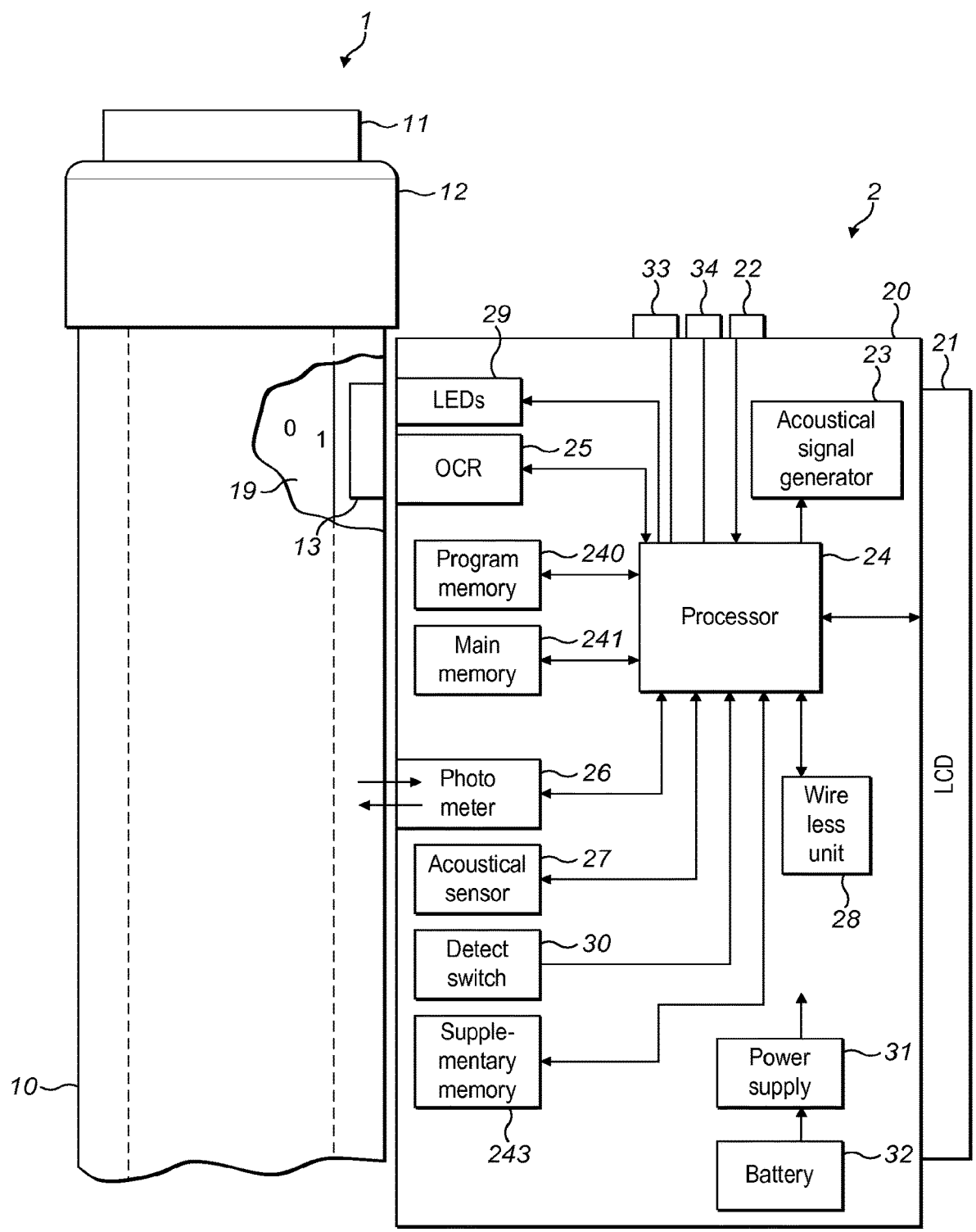

FIG. 3 shows a schematic view of the heretofore described supplemental devices in a state where they are attached to injection device 1 of FIG. 1a.

Within the housing 20 of the supplemental device 2 illustrated in FIG. 3, a plurality of components are comprised. These are controlled by a processor 24, which may for instance be a microprocessor, a Digital Signal Processor (DSP), Application Specific Integrated Circuit (ASIC), Field Programmable Gate Array (FPGA) or the like. Processor 24 executes program code (e.g. software or firmware) stored in a program memory 240, and uses a main memory 241, for instance to store intermediate results. A supplementary memory 243 may also be used to store a logbook on performed ejections/injections. Program memory 240 may for instance be a Read-Only Memory (ROM), main memory 241 may for instance be a Random Access Memory (RAM), and supplementary memory 243 may for instance be a flash memory. The supplementary memory 243 may comprise part of the supplemental device 2 or may alternatively be removably couplable thereto by a USB-type interface for instance or other connection.

In embodiments such as those shown in FIG. 2b, processor 24 interacts with a first button 22, via which supplemental device 2 may for instance be turned on and off. A second button 33 is a communications button. The second button may be used to trigger establishment of a connection to another device, or to trigger a transmission of information to another device. A third button 34 is a confirm or OK button. The third button 34 can be used to acknowledge information presented to a user of supplemental device 2.

Processor 24 controls a display unit 21, which may be embodied as a Liquid Crystal Display (LCD). Display unit 21 is used to display information to a user of supplemental device 2, for instance on present settings of injection device 1, or on a next injection to be given. Display unit 21 may also be embodied as a touch-screen display, for instance to receive user input.

Processor 24 also controls an optical sensor 25, embodied as an Optical Character Recognition (OCR) reader, that is capable of capturing images of the dosage window 13, in which a currently selected dose is displayed by way of numbers printed on the sleeve 19 contained in injection device 1, which numbers are visible through the dosage window 13. OCR reader 25 is further capable of recognizing numbers from the captured image and to provide this information to processor 24. Alternatively, unit 25 in supplemental device 2 may only be an optical sensor, e.g. a camera, for capturing images and providing information on the captured images to processor 24. Then processor 24 is responsible for performing OCR on the captured images.

Processor 24 also controls light-sources such as light emitting diodes (LEDs) 29 to illuminate the dosage window 13, in which a currently selected dose is displayed. A diffuser may be used in front of the light-sources, for instance a diffuser made from a piece of acrylic glass. Furthermore, the optical sensor may comprise a lens system, for instance including two aspheric lenses. The magnification ratio (image size to object size ratio) may be smaller than 1, for instance the magnification ratio may be in the range of 0.05 to 0.5. In some embodiments the magnification ratio may be 0.15.

Processor 24 may further control a photometer 26 (if one is provided), that is configured to determine an optical property of the housing 10 of injection device 1, for example a colour or a shading. Alternatively a colorimeter or a colour sensor system may be used instead of a photometer 26.

Processor 24 further controls (and/or receives signals from) an acoustic sensor 27, which is configured to sense sounds produced by injection device 1 which may occur when a dose is dialled by turning dosage knob 12 and/or when a dose is ejected/injected by pressing injection button 11, and/or when a prime shot is performed. These actions are mechanically similar but sound differently (this may also be the case for electronic sounds that indicate these actions). Either the acoustic sensor 27 and/or processor 24 may be configured to differentiate these different sounds, for instance to be able to safely recognize that an injection has taken place (rather than a prime shot only).

Processor 24 may further control an acoustical signal generator 23 (if one is provided), which is configured to produce acoustical signals that may be related to the operating status of injection device 1 e.g. as feedback to the user. For example, an acoustical signal may be launched by acoustical signal generator 23 as a reminder for the next dose to be injected or as a warning signal in case of misuse. Acoustical signal generator may for instance be embodied as a buzzer or loudspeaker. In addition to or as an alternative to acoustical signal generator 23, also a haptic signal generator (not shown) may be used to provide haptic feedback, for instance by way of vibration.

Processor 24 may control a wireless unit 28, which is configured to transmit and/or receive information to/from another device in a wireless fashion. Such transmission may be based on radio transmission or optical transmission. The wireless unit 28 may be a Bluetooth transceiver. In other embodiments information may be transmitted/received over a wired or optical fibre type connection instead of wirelessly.

Processor 24 may receive an input from a pen detection switch 30 (if one is provided), which is operable to detect whether the pen 1 is present, i.e. to detect whether the supplemental device 2 is coupled to the injection device 1.

A battery 32 powers the processor 24 and other components by way of a power supply 31.

The supplemental device 2 of FIG. 3 is thus capable of determining information related to a condition and/or use of injection device 1. This information is displayed on the display 21 for use by the user of the device. The information may be either processed by supplemental device 2 itself, or may at least partially be provided to another device (e.g. a blood glucose monitoring system), for example via the wireless unit 28.

Figure 4A:
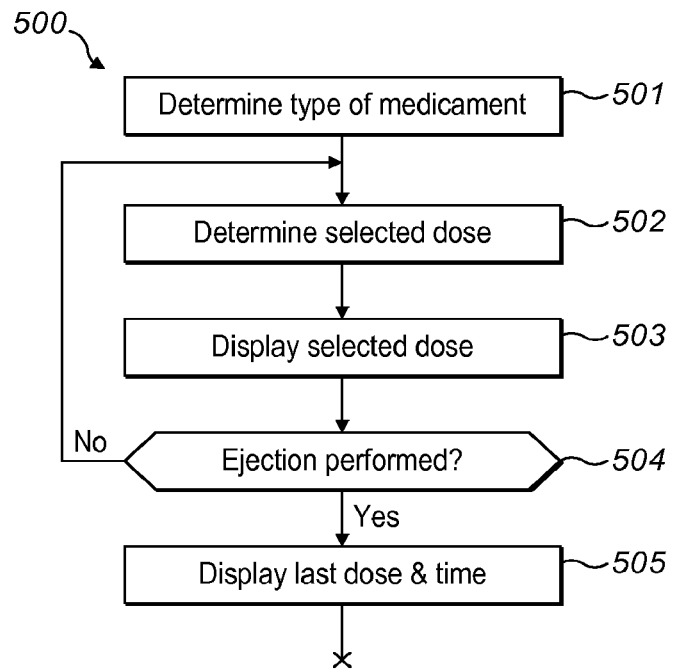
FIG. 4a: a flowchart of a method used in various embodiments.
Figure 4B:
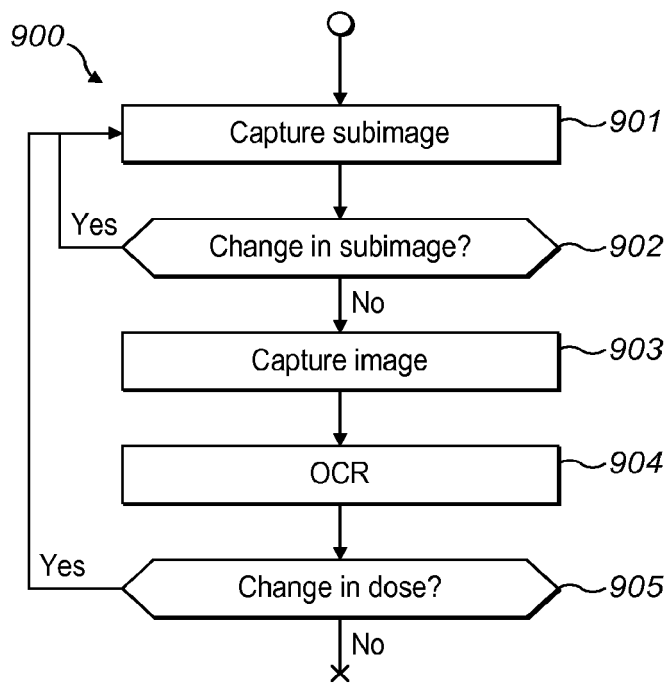
FIG. 4b: a flowchart of a further method used in various embodiments.

FIGS. 4a and 4b are flowcharts of embodiments of methods according to the present disclosure. These methods may be performed by processor 24 of supplemental device 2, and may for instance be stored in program memory 240, which may take the shape of tangible storage medium 600 of FIG. 5.

FIG. 4a shows method steps that are performed in scenarios where information is read by supplemental device 2 from injection device 1. The flowchart 500 starts when the supplemental device is turned on. In a step 501, a type of medicament, for example insulin, provided by the injection device is determined, e.g. based on colour recognition or on recognition of a code printed on the injection device. Detection of the type of medicament may not be necessary if a patient always takes the same type of medicament and only uses an injection device with this single type of medicament. Determination of the type of medicament may be ensured otherwise e.g. by a key-recess pair that the supplemental device is only useable with one specific injection device, which may only provide this single type of medicament.

In step 502, a currently selected dose is determined, e.g. by OCR of information shown in a dosage window of the injection device. This information is then displayed to a user of the injection device in a step 503.

In a step 504, it is checked if an ejection has taken place, e.g. by sound recognition as described above. Therein, a prime shot may be differentiated from an actual injection (into a creature) either based on respectively different sounds produced by the injection device and/or based on the ejected dose (e.g. a small dose less than a pre-defined amount, e.g. 4 or 3 units, may be considered to be a prime shot, whereas larger doses are considered injections).

If an ejection has taken place, the determined data, i.e. the selected dose and—if applicable—the type of medicament (e.g. insulin), is stored in the main memory 241 and/or the supplementary memory 243, from where it may later be transmitted to another device, for instance a blood glucose monitoring system via the wireless unit 28. If a differentiation has been made concerning the nature of the ejection, e.g. if the ejection was performed as a prime shot or as an actual injection, this information may also be stored in the main memory 241 and/or the supplementary memory 243, and later transmitted. In the case of an injection having been performed, at step 505 the dose is displayed on the display 21. Also displayed is a time since the last injection which, immediately after injection, is 0 or 1 minute. The time since last dose may be displayed intermittently. For instance, it may be displayed alternately with the name or other identification of the medicament that was injected, e.g. Apidra or Lantus.

If ejection was not performed at step 504, steps 502 and 503 are repeated.

After display of the delivered dose and time data, flowchart 500 terminates.

FIG. 4b shows in more detail exemplary method steps that are performed when the selected dose is determined based on the use of optical sensors only. For instance, these steps may be performed in step 502 of FIG. 4a.

In a step 901, a sub-image is captured by an optical sensor such as optical sensor 25 of supplemental device 2. The captured sub-image is for instance an image of at least a part of the dosage window 13 of injection device 1, in which a currently selected dose is displayed. For instance, the captured sub-image may have a low resolution and/or only show a part of sleeve 19 which is visible through dosage window 13. For instance, the captured sub-image could show the numbers printed on the part of sleeve 19 visible through dosage window 13. After capturing an image, it is, for instance, further processed as follows:

Division by a previously captured background image;
Binning of the image(s) to reduce the number of pixels for further evaluations;
Normalization of the image(s) to reduce intensity variations in the illumination;
Sheering of the image(s); and/or
Binarization of the image(s) by comparing to a fixed threshold.

Several or all of these steps may be omitted if applicable, for instance if a sufficiently large optical sensor (a sensor with sufficiently large pixels) is used.

In step 902, it is determined whether or not there is a change in the captured sub-image. The currently captured sub-image may be compared to the previously captured sub-image(s) in order to determine whether or not there is a change. Therein, the comparison to previously captured sub-images may be limited to the sub-image of the previously captured sub-images that was captured immediately before the current sub-image was captured and/or to the sub-images of the previously captured sub-images that were captured within a specified period of time (e.g. 0.1 seconds) before the current sub-image was captured. The comparison may be based on image analysis techniques such as pattern recognition performed on the currently captured sub-image and on the previously captured sub-image(s). It may be analyzed whether the pattern of the number(s) visible through the dosage window 13 and shown in the currently captured sub-image and in the previously captured sub-image(s) is changed. It may be searched for patterns in the image that have a certain size and/or aspect ratio and these patterns may be compared with one or more previously saved patterns. Steps 901 and 902 may correspond to a detection of a change in the captured image.

If it is determined in step 902 that there is a change in the sub-image, step 901 is repeated. Otherwise in a step 903, an image is captured by an optical sensor such as optical sensor 25 of supplemental device 2. The captured image is for instance an image of the dosage window 13 of injection device 1, in which a currently selected dose is displayed. The captured image may have a resolution being higher than the resolution of the captured sub-image. The captured image at least shows the number(s) printed on the sleeve 19 of injection device 1 which are visible through the dosage window 13.

In step 904, optical character recognition is performed on the image captured in step 903 to recognize the number(s) printed on the sleeve 19 and visible through the dosage window 13, since the number(s) correspond to the (currently) selected dose. In accord to the recognized numbers, the selected dose is determined.

In step 905, it is determined whether or not there is a change in the determined selected dose and, optionally, whether or not the determined selected dose does not equal zero. The currently determined selected dose may be compared to the previously determined selected dose(s) in order to determine whether or not there is a change. Therein, the comparison to previously determined selected dose(s) may be limited to the previously determined selected dose(s) that were determined within a specified period of time (e.g. 3 seconds) before the current selected dose was determined. If there is no change in the determined selected dose and, optionally, the determined selected dose does not equal zero, the currently determined selected dose is returned/forwarded for further processing (e.g. to processor 24).

Thus, the selected dose is determined if the last turn of the dosage knob 12 is more than 3 seconds ago. If the dosage knob 12 is turned within or after these 3 seconds and the new position remains unchanged for more than 3 seconds, this value is taken as the determined selected dose.

Figure 5:
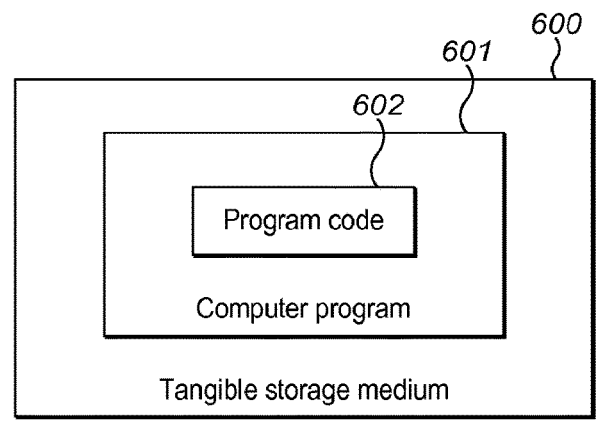
FIG. 5: a schematic illustration of a tangible storage medium.

FIG. 5 is a schematic illustration of a tangible storage medium 600 (a computer program product) that comprises a computer program 601 with program code 602. This program code may be executed by processors contained in the supplemental device, for instance processor 24. Storage medium 600 may represent program memory 240 of supplemental device 2 and may be a fixed memory or a removable memory (e.g. a memory stick or card).

How the supplemental device 2 and injection device 1 in FIG. 3 may be coupled together will now be described with reference to FIGS. 6 to 12.

Figure 6:
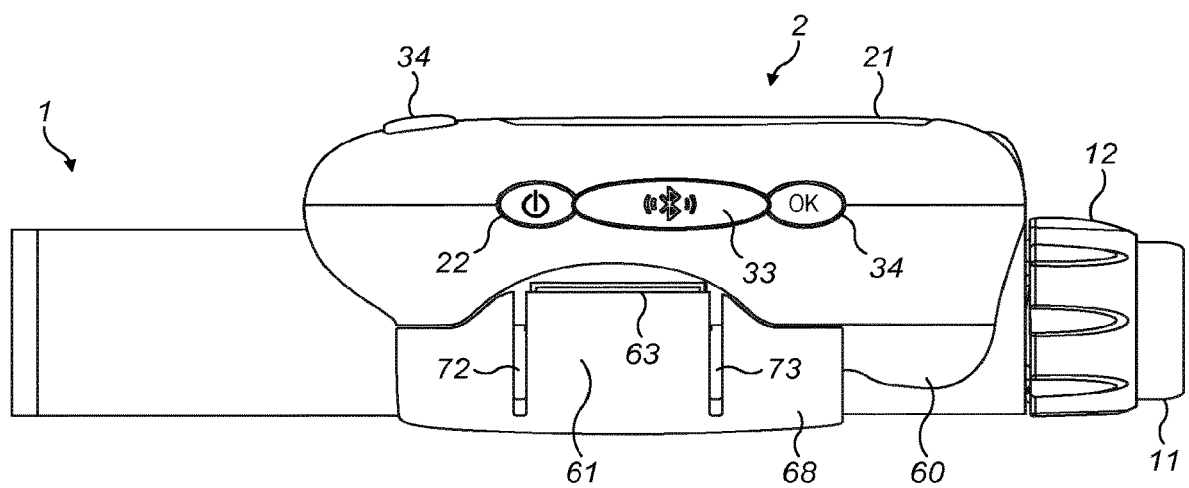

As is best seen from FIG. 6, the supplemental device 2 is attached to the injection device 1 close to the dosage knob 12 with the display 21 uppermost in the orientation shown (which is the same for all of FIGS. 6 to 12). The plane of the display 21 lies generally transverse to the longitudinal axis of the injection device 1, and is perpendicular to the page of FIGS. 6, 7, 8, 10, 11 and 12.

A closure 68 extends from a shaft 59 of a hinge, the closure extending underneath the injection device. The closure 68 is connected to the supplemental device 2 on the right side (looking at the injection device 1 with the injection button closest to the viewer), extends underneath the injection device 1 and connects with the supplemental device on the left side thereof.

The supplemental device 2 includes two features that contribute to correct alignment of the supplemental device 2 on the injection device 1, and one feature that results in securing of the supplemental device 2 to the injection device 1. The features that contribute to correct alignment of the supplemental device 2 on the injection device 1 can be termed alignment arrangements. The features that contribute to securing of the supplemental device 2 to the injection device 1 can be termed a securing arrangement.

The correct alignment of the supplemental device 2 on the injection device 1, ensures that the OCR reader 25 is correctly aligned with the dosage window 13. Correct alignment allows correct operation and reliable readings. Ensuring that there can be correct alignment between the supplemental device 2 and the injection device 1 in use allows a simpler design for the OCR reader 25, in particular because it does not need to be designed to be able to accommodate different alignments between the devices 1, 2.

Figure 9A:
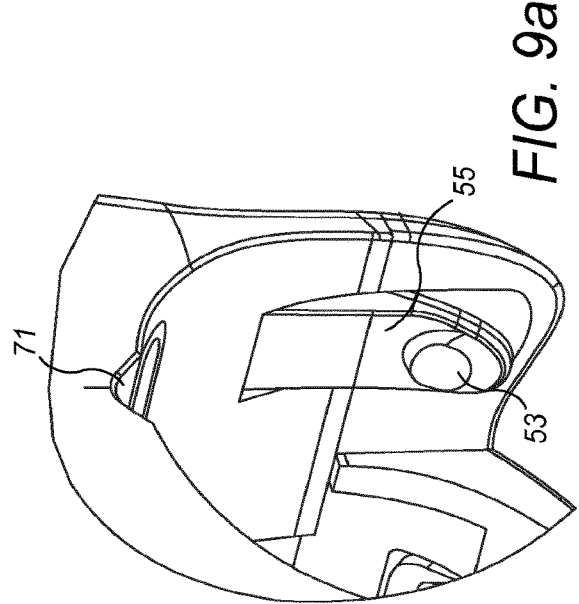
FIG. 9a: a partial cutaway perspective view of a detail from FIG. 8.
Figure 9B:
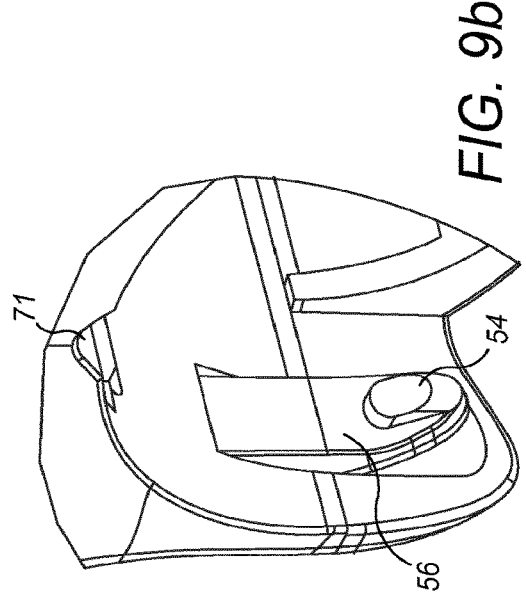
FIG. 9b: a partial cutaway perspective view of another detail from FIG. 8.

The first alignment feature is a locating channel 71 (see FIG. 9a). The locating channel 71 is located at the uppermost part of an injection device receiving channel 58 that is defined between the main body of the supplemental part and the closure 68 when in the closed position. The locating channel 71 is best shown in FIGS. 9a and 9b. From here, it will be seen that the locating channel is formed at the end of the supplemental device that is closest to the dosage knob 12 when the supplemental device 2 is fitted to the injection device 1.

As is best seen in FIG. 1b, the locating rib 70 is located between the display window 13 and the dosage knob 12. In this example, the locating rib 70 extends for the whole of the distance between the display window 13 and the dosage knob 12. In other examples, the locating rib is shorter. The locating rib 70 is taller at the end that is adjacent the dosage knob 12 and tapers down to a zero height at the junction with the display window 13. As can be seen from FIG. 1b, the taper of the uppermost edge of the locating rib 70 is slightly curved. The gradient of the taper is less at the part of the locating rib 70 that is closest to the dosage knob 12 and is greater along the locating rib to the location of the display window 13. The shape of the locating rib 70 is such that the gradient continually increases as one moves from the position of the locating rib 70 that is adjacent to the dosage knob 12 to the position of the locating rib 70 that is adjacent the display window 13.

The thickness of the locating rib 70, the thickness being the dimension that is circumferential to the main body of the injection device 1, varies along the length of the locating rib 70. The thickness of the locating rib 70 is greatest at the end adjacent the dosage knob 12 and is least at the end adjacent the display window 13. The thickness of the locating rib 70 gradually decreases as one moves from the end of the locating rib adjacent the dosage knob 12 to the end of the locating rib that is adjacent the display window 13.

The cross-section of the locating rib, the cross-section being a section taken perpendicular to the longitudinal axis of the injection device 1, is of a rounded triangle. The cross-section of the locating rib 70 is approximately the same for its entire length, although of course the size varies.

The locating channel 71 is dimensioned so as to correspond closely to the shape and size of the locating rib 70 that is present on the injection device 1.

The locating channel 71 has a size and shape that corresponds closely to the size and shape of the locating rib 70.

The locating channel 71 is slightly larger than the locating rib so as to ensure that the locating rib can be located within the locating channel 71. When the locating rib 70 is within the locating channel 71, the corresponding sizes ensure that the two features mate together. This assists in ensuring correct positioning of the supplemental device 2 on the injection device 1.

Other features of the supplemental device 2 and the injection device 1 that assist in ensuring correct alignment between the two devices will now be described. As best seen in FIG. 1b, the injection device 1 is provided with indents on either side of its body at locations close to the dosage knob 12. In FIG. 1b, a left side indent 52 is shown. A right indent 51, which is shown in FIG. 8, is located in a corresponding position on the right side of the injection device 1.

The left and right indents 51, 52 are relatively shallow depressions. The indents 51, 52 have sloping sides, that is the sides of the indents 51, 52 are not parallel. Also, they are not radial with respect to the longitudinal axis of the injection device 1. In these embodiments, the slope of the sides of the left and right indents 51, 52 is different for different parts of the indents. In particular, the gradient of the slope of the sides of the indents is less at the part of the indents that is furthest from the display window 13 and is greatest at the part of the indents 51, 52 that is closest to the display window 13. In these examples, the slope of the indents changes between these two extremes, for instance in a linear fashion.

The slope of the sides of the indent may for instance be between 30 and 70 degrees at the part that is furthest from the display window 13. The slope may for instance be between 60 and 80 degrees for the part that is closest to the display window 13. The greater angle of slope at the part closer to the display window 13 aids engagement of a face of a protuberance within the indent 51, 52 in such a way as to provide some resistance against removal of the supplemental device 2 in a direction radial to the longitudinal axis of the injection device 1.

Figure 8:
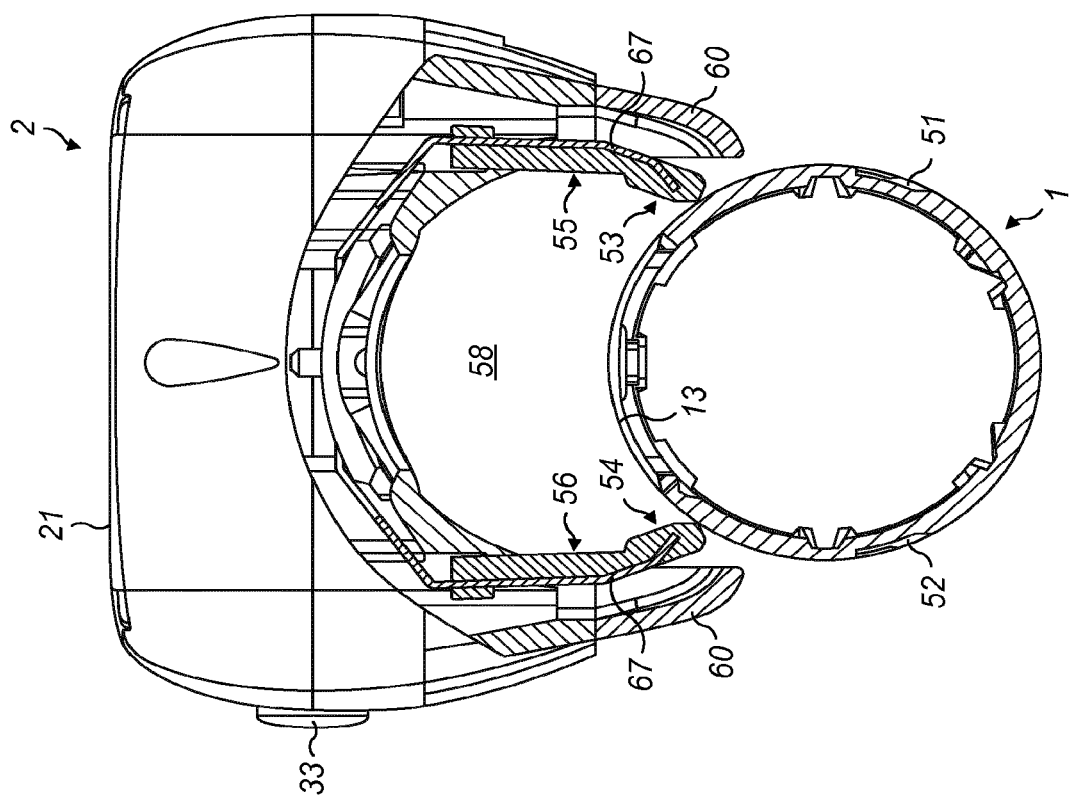
FIG. 8: a cross-sectional view through the arrangement of the supplemental device and the injection device of FIG. 6 prior to engagement of the supplemental device on the injection device.

As is best seen in FIGS. 8, 9a and 9b, the left and right protuberances 53, 54 are shaped to correspond to the shapes of the right and left indents 51, 52 respectively. In this way, the right and left protuberances 53, 54 fit within the right and left indents 51, 52 respectively when the supplemental device 2 is correctly positioned on the injection device 1. The external dimensions of the right and left protuberances 53, 54 are slightly smaller than the internal dimensions of the right and left indents 51, 52 so as to ensure that the protuberances fit within their respective indent.

In these embodiments, the protuberance 53 is shaped to correspond closely to the shape of the indent 51. In this way, the protuberance 53 fits snugly within the indent 51 when the supplemental device 2 is correctly positioned on the injection device 1. The protuberance 54 is shaped similarly to the protuberance 53, although it is less tall. Put another way, it is like the protuberance 53 but with the top part missing or cut off. This is the reason for the end face of the protuberance 54 having a larger area than the protuberance 53. The different sizes for the protuberances 53, 54 helps the protuberances find engagement within the indents 51, 52. The protuberance 53 can be considered to be a master to the other protuberance, which is a slave.

The right protuberance 53 is located at the end of the right arm 55, which is best shown in FIG. 9a. As can be seen from FIG. 9b, the left protuberance 54 is located at the end of the left arm 56. As can be best seen from FIG. 8, the right and left arms 55, 56 depend substantially vertically from the body of the supplemental device 2. The right and left arms 55, 56 are thus formed either side of the injection device receiving channel 58.

A biasing feature 67, in the form of a substantially u-shaped spring, is coupled to each of the right and left arms 55, 56. The effect of the biasing feature 67 is to bias the right and left arms into a certain position. The position into which the right and left arms 55, 56 are biased is such that the distance between the innermost surfaces of the right and left protuberances 53, 54 is slightly less than the distance between the bottoms of the right and left indents 51, 52. The effect of the biasing feature 67 is to resist movement of the protuberances 53, 54 and the arms 55, 56, away from one another.

Alternatively, instead of a biasing feature 67 skilled persons will realise that a compression spring may be located in the space between the flaps 60 and the respective arms 55, 56 to resist movement of the protuberances 53, 54 and the arms 55, 56, away from one another.

Because the slopes of the sides of the protuberances 53, 54 match the sides of the indents 51, 52, the sloped sides of the protuberances 53, 54 at the distal ends of the arms 55, 56 is relatively shallow. This assists in sliding the protuberances 53, 54 over the external surface of the body 10 of the injection device 1 as the supplemental device is being fitted. This is best demonstrated with reference to FIGS. 8 and 10.

As is shown in FIG. 8, the supplemental device 2 is located with respect to the injection device 1 such that the ends of the right and left arms 55, 56, in particular the protuberances 53, 54, are just touching the housing 10 of the injection device 1. The protuberances 53, 54 here contact the housing to the left and right sides of the display window 13.

The left and right arms 55, 56 are present behind flaps 60 that depend from the supplemental device 2 on both the left and right sides. As can be seen from FIG. 8, the flaps, or protecting walls 60, extend slightly further in a downwards direction than the arms. The flaps 60 are formed of transparent material. This allows a user to be able to view the locations of the arms 55, 56 relative to the indents 51, 52, which may help them to locate the supplemental device 2 correctly on the injection device 1.

In order to mate the supplemental device 2 with the injection device 1, the user first arranges the supplemental device 2 with respect to the injection device 1 as shown in FIG. 8, and then applies a force downwards on the supplemental device 2 while at the same time applying a force upwards on the injection device 1. This places force on the protuberances 53, 54, and thus the right and left arms 55, 56. As the injection device 1 and the supplemental device 2 move closer together, the force results in the arms being moved apart, against the resilience of the spring 67 which causes spring 67 to apply a reaction force that resists entry of the injection device 1 into the injection device receiving channel 58. However, when the protuberances 53, 54 reach the location on the injection device 1 at which they are directly in line with the longitudinal axis of the injection device, the reaction force supplied by the spring 67 ceases to increase upon further movement of the injection device 1 and supplemental device 2 together. After this point, movement of the injection device 1 into the injection device receiving channel 58 is aided by the resilience of the spring 67.

After some further movement, the protuberances 53, 54 become aligned with the left and right indent 51, 52 and, due to the resilience of the spring 67, become engaged with the indents. Engagement provides haptic and audio feedback as the protuberances 53, 54 click or snap into the indents 51, 52. The feedback is enhanced by the force provided by the resilience of the spring 67. Once the protuberances 53, 54 are mated with the indents 51, 52, there is significant resistance to further movement of the supplemental device 2 relative to the injection device 1, due in part to the corresponding shapes of the protuberances 53, 54 and the indents 51, 52 and due in part to the biasing together of the arms 55, 56 by the spring 67.

Figure 10:
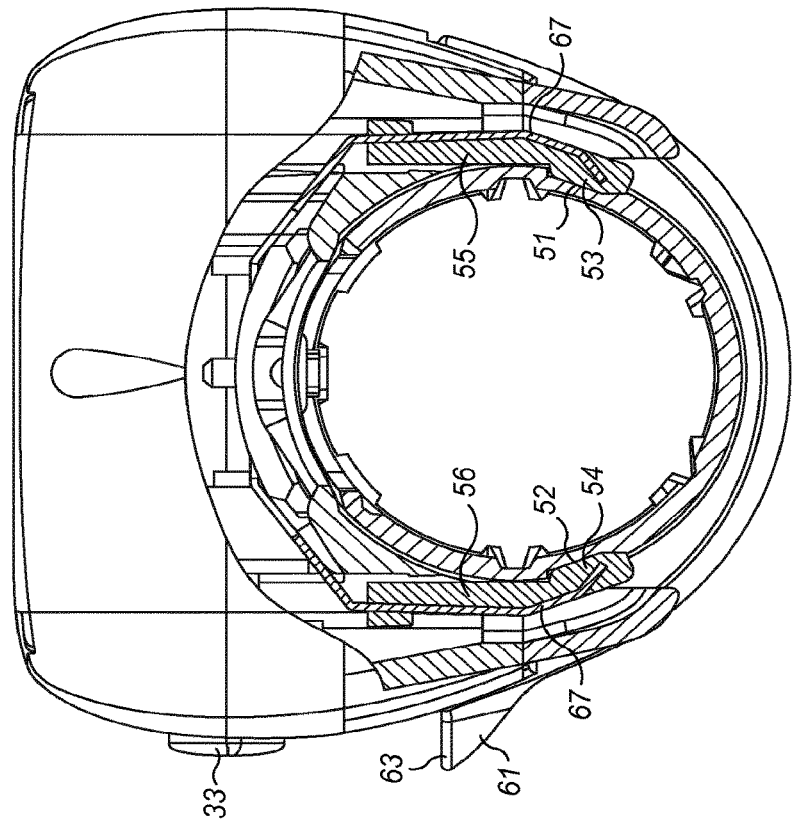
FIG. 10: a cross-sectional view which is the same as FIG. 8 although with the supplemental device mated to the injection device.

Once the protuberances 53, 54 are mated in the indent 51, 52, the injection device 1 is fully located within the injection device receiving channel 58 as shown in FIG. 10. Here, it will be seen that the outermost surface of the display window 13 is generally aligned with a lowermost surface of the upper part of the supplemental device 2. This supplemental device 2 is shaped such that the injection device 1 fits snugly within the injection device receiving channel 58 and there are multiple points or areas of contact between the exterior surface of the housing 10 of the injection device 1 and the lowermost surface of the supplemental device 2 when the supplemental device and the injection device 1 are in this relative position. Even in the absence of the mating of the protuberances 53, 54 with the indents 51, 52 at this point, the user would notice that there is a natural tendency for the injection device 1 to sit at this location within the supplemental device 2.

When the supplemental device 2 is located with respect to the injection device 1 such that the right and left protuberances 53, 54 are located within the right and left indents 51, 52 respectively, the locating rib 70 is engaged within the locating channel 71. Correct alignment of the supplemental device 2 with respect to the injection device 1 is thus provided in two ways: firstly, by the location of the locating rib 70 within the locating channel 71 and secondly by the locating of the protuberances 53, 54 within the indents 51, 52.

In the event that the user places the supplemental device 2 onto the injection device 1 at a location such that the supplemental device 2 is slightly at the right of the position shown in FIG. 6, the locating rib 70 does not fit within the locating channel 71. In this case, the supplemental device 2 is prevented from being located fully over the injection device 1 by the locating rib 70 resting against a surface of the supplemental device 2 that is in some way distal from the correct location within the locating channel 71. However, in this position, the ends of the protuberances 53, 54 have passed the halfway point of the circumference of the housing 10 of the injection device 1 and thus the spring 67 results in the injection device 1 being biased towards the supplemental device 2 so as to be located within the injection device receiving channel 58. A user would know that the supplemental device 2 had not mated correctly with the injection device 1 because they would not have received any haptic feedback from the mating of the protuberances 53, 54 with the indents 51, 52. They would also notice that the end of the supplemental device that is closest to the dosage knob 12 was separated from the injection device 1 by a distance greater than the separation of the supplemental device 2 from the injection device 1 at the end of the supplemental device 2 distal from the dosage knob 12. In this situation, the user can engage the supplemental device 2 and the injection device 1 simply by exerting a force against the supplemental device 2 and the injection device 1 such as to move the supplemental device 2 leftwards in the direction shown in FIG. 6. As the supplemental device 2 and the injection device 1 move relative to one another, the locating rib and the locating channel become more and more engaged. The spring force provided by the spring 67 may assist relative movement of the supplemental device 2 and the injection device 1 in this manner. As the locating rib 70 and the locating channel 71 become more engaged, the end of the supplemental device 2 that is closest to the dosage knob 12 moves down towards the injection device 1. This movement continues until the locating rib 70 is completely within the locating channel 71, at which point the right and left protuberances 53, 54 also engage with the right and left indents 51, 52 respectively. At this point, haptic feedback is provided by the mating of the protuberances 53, 54 with the indents 51, 52 and the user can determine that the supplemental device 2 and the injection device 1 are properly located with respect to one another.

If the user locates the supplemental device onto the injection device 1 such that the supplemental device is to the left of the position shown in FIG. 6, mating between the supplemental device 2 and the injection device 1 will not occur. In this case, the locating rib 70 will not prevent the supplemental device 2 from being located flat against the injection device 1. A user, noticing this, will know that the supplemental device 2 is located too far from the dosage knob 12. The user can engage the supplemental device 2 with the injection device 1 simply by moving the supplemental device 2 relative to the injection device 1 such as to move the supplemental device 2 rightwards in the direction in FIG. 6.

The supplemental device 2 may be provided with a closure 68, which has a primary function of clamping the supplemental device 2 to the injection device 1 when the two devices are mated with one another.

Figure 12:
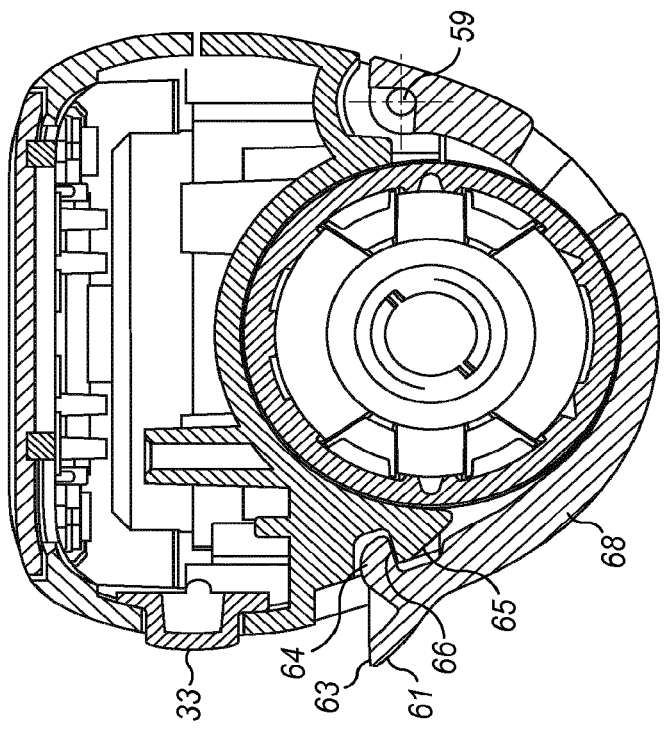
FIG. 12: the same cross-section as shown in FIG. 11 although with the supplemental device installed on an injection device and clamped in place.
Figure 11:
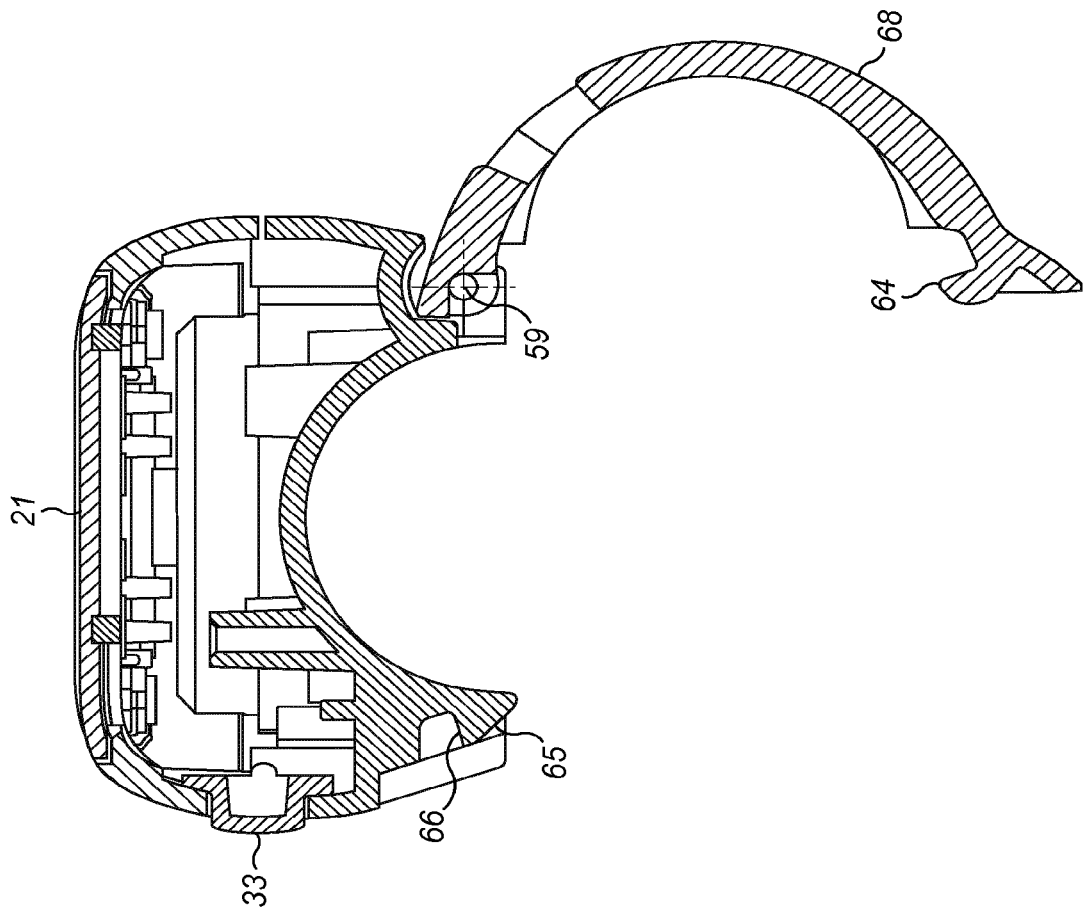
FIG. 11: a cross-sectional view through the supplemental device of FIG. 2b at a location further along the device from the cross-section shown in FIG. 8.

As best seen in FIGS. 11 and 12, the closure 68 has an innermost surface that coincides with the curved surface of an imaginary cylinder. The diameter of the cylinder is the same as the external dimension of the housing 10 of the injection device 1. As such, the closure 68 forms a snug fit against the lowermost part of the housing 10 of the injection device 1 when the supplemental device 2 is in place on the injection device 1.

The closure 68 is moveable between an open position, shown in FIG. 11, and a closed position, shown in FIG. 12.

As can be seen in FIG. 6, the closure 68 is located next to the arm protecting walls 60, in a direction opposite the arm protecting walls 60 to the dosage knob 12. The closure 68 has a dimension in a longitudinal axis of the injection device 1 that may be approximately 60% of the length dimension of the supplemental device 2.

The material of the closure 68 has a generally uniform thickness. As such, the external surface of the closure 68, that is the surface that is furthest from the longitudinal axis of the injection device 1 when the supplemental device 2 is mated with the injection device 1, is generally cylindrical, or at least takes the form of part of a cylinder.

Figure 7:
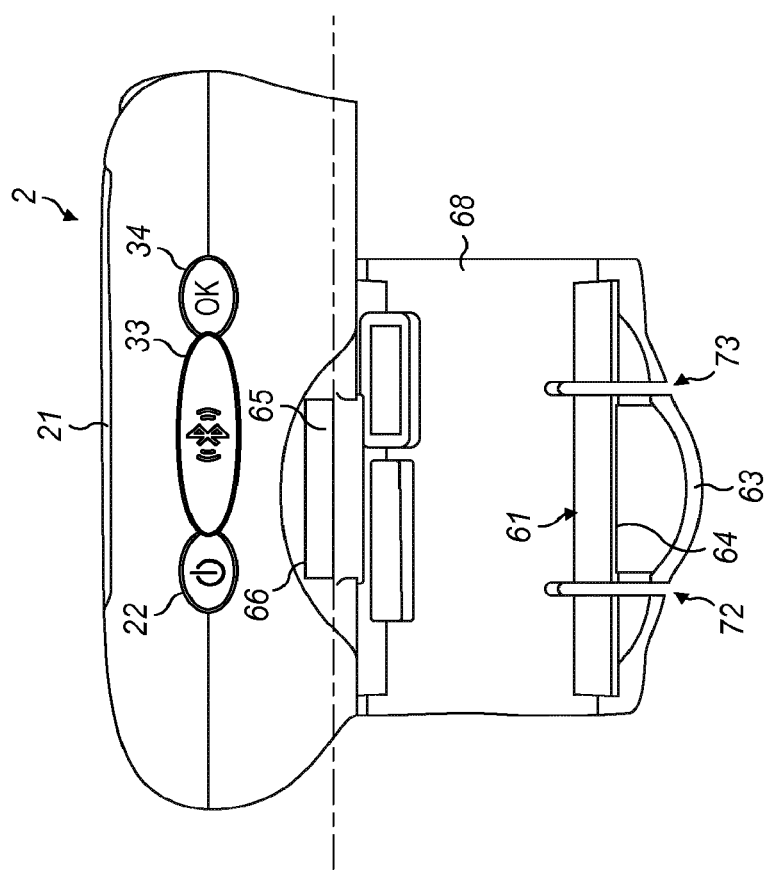
FIG. 7: a side view of the supplemental device in the same view as FIG. 6 although with the injection device omitted and with a closure open.

The closure 68 is provided with two cutaways 72, 73. The cutaways 72, 73 extend from an edge of the closure 68 that is furthest from the shaft 59 of the hinge formed at the other side of the supplemental device 2. The cutaways 72, 73 extend from this edge in a direction that is generally circumferential with respect to the injection device 1. The length of the cutaways is approximately equal to ⅙ or ⅕ of the circumference of the circle on which the closure 68 generally lies. The cutaways 72, 73 define a tab 61. The tab 61 is connected to the main part of the closure 68 at a location between the lowermost ends of the cutaways 72, 73. A free end 63 of the tab 61 is located between the uppermost ends of the cutaways 72, 73. As is best seen in FIG. 7, the free end 63 of the tab 61 is curved so as to extend away from the longitudinal axis of the injection device 1 by a greater extent at a point that is central between the cutaways 72, 73. This allows a user better to be able to locate a digit on the free end 63 of the tab 61 so as to be able to pull the free end 63 in a direction that is downwards and leftwards in FIG. 12.

On the inside surface of the tab 61 is provided a latching edge 64. The latching edge 64 is provided at a junction between a latching face and another face. The latching edge 64 extends for the width of the tab 61. The latching face is in a plane that extends approximately radially with respect to the longitudinal axis of the injection device 1 when the closure 68 is in the closed position, as shown in FIG. 12. In this position, the latching edge 64 is engaged with a latch engaging face 66 that is provided as a part of the uppermost portion of the supplemental device 2, i.e. is provided as a portion of the supplemental device 2 that is not part of the closure 68. The latch engaging face 66 is provided in a plane that is generally the same orientation as the plane of the latching face when the closure 68 is in the closed position.

When the user has mated the supplemental device 2 onto the injection device 1, in particular mating the locating rib 70 within the locating channel 71 and locating the protuberances 53, 54 within the indents 51, 52, the user may secure the supplemental device 2 to the injection device 1. This is achieved by the user moving the closure 68 from the position shown in FIG. 11, in which the injection device receiving channel 58 is open for inclusion of the injection device 1 therein, and rotating the closure 68 around the shaft 59 of the hinge so as to move the free end 63 of the tab 61 towards the latch engaging face. Movement continues until contact is made between the innermost part of the latching edge 64 against a guide surface 65, which is located just beneath the latch engaging face 66. The guide surface 65 is angled approximately tangentially to the outside surface of the housing 10 of the injection device 1.

At this point, the tendency of the closure 68 to adopt the shape shown in FIG. 11 provides a spring force between the end of the tab 61 and the guide surface 65. As the user exerts further force against the closure 68, the closure 68 deforms resiliently so as to increase the separation between the free end 63 of the tab 61 and the hinge 59. This allows the edge of the latching edge 64 to slide over the guide surface 65. This continues until the latching edge 64 becomes aligned with the edge between the guide surface 65 and the latch engaging face 66, at which point the latching edge 64 and the latching face engage within the channel that is formed against the latch engaging face 66. At this point, the resilience of the closure 68 results in the latching edge 64 and the latch engaging face 66 becoming engaged with one another, and at this point the components are in the position shown in FIG. 12. In this position, it will be seen that the innermost surface of the closure 68 is snug against the outermost surface of the housing 10 of the injection device 1. At this point, the closure 68 ensures that the injection device 1 is tightly contained within the injection device receiving channel 58 and is held in place by the closure 68.

Other configurations of both coupling and alignment features are envisaged. For instance, in some embodiments, the locating rib 70 and the locating channel 71 are absent. In these embodiments, the correct alignment between the supplemental device 2 and the injection pen device 1 is provided by mating of the protuberances 53, 54 and the indents 51, 52. In some other embodiments, the right and left arms 55, 56 and the protuberances 53, 54 are absent. In these embodiments, the correct alignment between the supplemental device 2 and the injection device 1 is provided by the locating rib 70 and the locating channel 71. Other alternative arrangements for ensuring a correct relative position between the supplemental device 2 and the injection device 1 will be envisaged by the skilled person. Also, the skilled person will be aware of alternative securing arrangements, for instance clamping, the supplemental device 2 to the injection device 1 once the correct relative position has been attained.

Details of an exemplary optical arrangement that enables optical character recognition to be implemented as heretofore described will now be set out.

Figure 13:
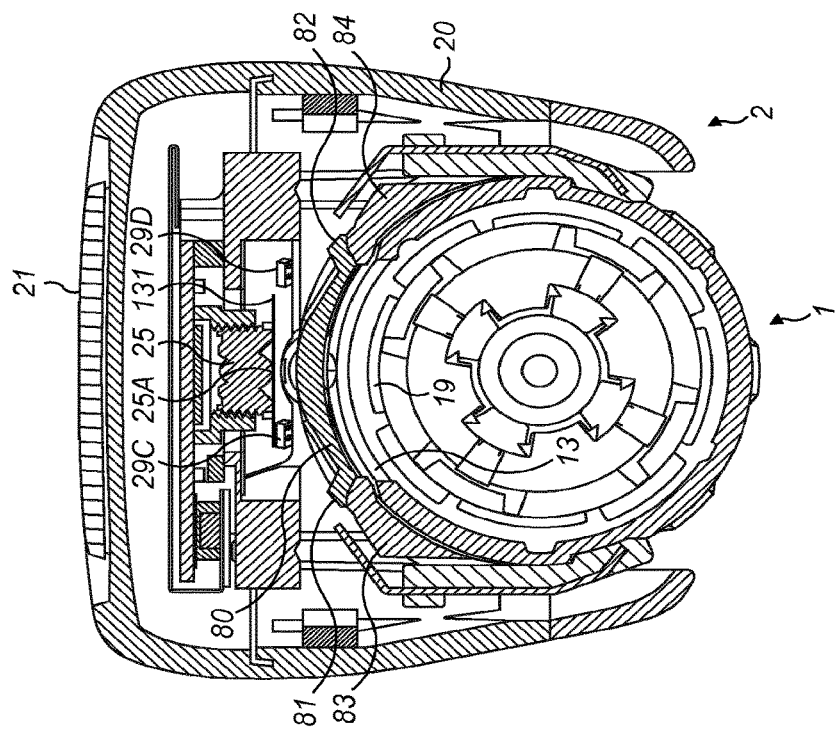
FIG. 13: a cross-sectional view through the supplemental device when installed on an injection device, the cross-section being through a camera and optical system.

FIG. 13 is a cross-sectional view through a supplemental device 2 and an injection device 1 in a direction perpendicular to the axis of the injection device 1. The cross-section is through the optical sensor 25. In FIG. 13, the supplemental device 2 is engaged with the injection device 1, forming a snug fit therewith. Moreover, the supplemental device 2 and the injection device 1 are aligned correctly, by virtue of the mating of the protuberances 53, 54 in the indents 51, 52 and the mating of the alignment rib 70 and the alignment channel 71. In this position, the optical sensor 25 is directed at the dosage window 13. In particular the optical sensor 25 comprises a camera for generating camera output indicative of a scene in the field of view thereof, and will be referred to as a camera hereafter.

The camera 25 in FIG. 13 may comprise part of an Optical Character Recognition (OCR) reader. For instance the camera 25 may be used to capture images of a dosage window 13 of an injection device 1 in which a currently selected dose is displayed. Such images comprise camera output and are indicative of information appearing on the dosage sleeve 19 as it appears in the field of view of the camera 25. The OCR reader of which the camera 25 comprises part may process these images and recognize numbers from the captured images and provide this information to a central processor, such as the processor 24 in FIG. 3. Alternatively however, the camera 25 may be configured to provide camera output directly to a central processor, e.g. processor 24 which then processes the images and performs OCR thereon.

Numbers on the dosage sleeve 19 of the injection device 1 may be printed in fluorescent material. A fluorescent material is one that emits fluorescence (or in other words, one that fluoresces) when illuminated with light of a particular frequency. When such material is illuminated with light of a particular frequency it absorbs the light and subsequently emits light having another, different, frequency. The supplemental device 2 comprises a plurality of light sources (e.g. LEDs) 29a-29d which are controllable by the processor 24 to illuminate the number(s) aligned with the dosage window 13 of the injection device 1, thereby causing the number(s) to emit fluorescence. The supplemental device 2 uses this fluorescence to perform OCR. Looking again at FIG. 13 a filter 131 is provided which extends across the whole of the field of view of the optical sensor 25 and is configured to block light of the same frequency as that emitted by the light sources 29a-29d, while at the same time being substantially transparent to light emitted as fluorescence from the dosage sleeve 19. The filter 131 may comprise glass or polymer film. In both of these alternatives the filter 131 may be provided with, or house, a layer of absorbing dye that is configured to block and transmit the necessary wavelengths of light heretofore mentioned. Alternatively or in addition, the glass or polymer film may be coupled to an interference filter.

In other words, the light sources 29a-29d are controllable by the processor 24 to illuminate the dosage sleeve 19 of an injection device 1 with optical illumination, so that material which defines numbers on the dosage sleeve 19 is caused to emit optical fluorescence that can be detected by the camera 25. The camera 25 then generates camera output, indicative of a scene in the field of view thereof, on the basis of the detected optical fluorescence.

A fuller discussion of the optical arrangement in FIG. 13 will now be provided.

In FIG. 13 it can be seen that the dosage window 13 is of even thickness in cross-section and has a shape that forms part of a cylindrical annulus. The axis of the cylinder on which the dosage window 13 falls is the axis of the injection device 1. The dosage window 13 may be slightly conical in the axial direction.

A protection window 80 may be located between the camera 25 and the dosage window 13. The protection window 80 includes a lowermost surface that falls on the curved surface of a cylinder having an axis aligned with the axis of the injection device 1. The uppermost surface of the protection window 80 has a smaller radius. Thus, the protection window 80 has a greater thickness at its central part, which is in the path directly between the camera 25 and the axis of the injection device 1, than it does at its edges. Thus, the protection window 80 has optical power. The protection window 80 is configured such that it forms part of the imaging system of the camera 25, along with the lens 25a. The lens 25a in these embodiments has two lenses, referred to as a lens for ease of explanation. The optical power of the protection window 80 allows a short track length and contributes to a compact arrangement.

In other embodiments, the protection window 80 does not have optical power, or put another way has zero optical power. Such arrangements may function equally well but may be less compact.

The protection window 80 may be formed of any suitable optically transparent material. For instance, the protection window is formed of optics grade plastics, for instance optics grade polycarbonate or PMMA (polymethyl methacrylate acrylic).

At the left edge of the window 80 is provided a feature 81 that connects with a left window support 83 that forms part of the body 20 of the supplemental device 2. A feature 82 on the right edge of the window is similarly configured to rest against a right window support 84 that forms part of the body 20 of the supplemental device 2. The left and right window supports 83, 84 serve to support the protection window 80 in a correct location with respect to other components of the supplemental device 2.

The protection window 80 is sealed with respect to the body. This prevents the ingress of dirt, dust and other debris into the body 20 and thus helps to maintain correct operation of the camera 25 and other parts of the optical system. Thus, the protection window 80 forms part of the mechanical configuration of the body 20 of the supplemental device 2 as well as part of the optical system. This helps to allow compactness in the overall arrangement.

As is best seen in FIG. 1a, the dosage window 13 is not square with respect to the injection device 1. Instead, the dosage window is at an angle, which allows the dosage sleeve 19 to provide numbers in a helical fashion, the numbers appearing in the dosage window 13 as the dosage dial 12 is rotated by a user and a dose is delivered. In the SoloStar injection device sold by Sanofi, the dosage window 13 and the numbers on the dosage sleeve 19 are inclined at 13 degrees.

Figure 15:
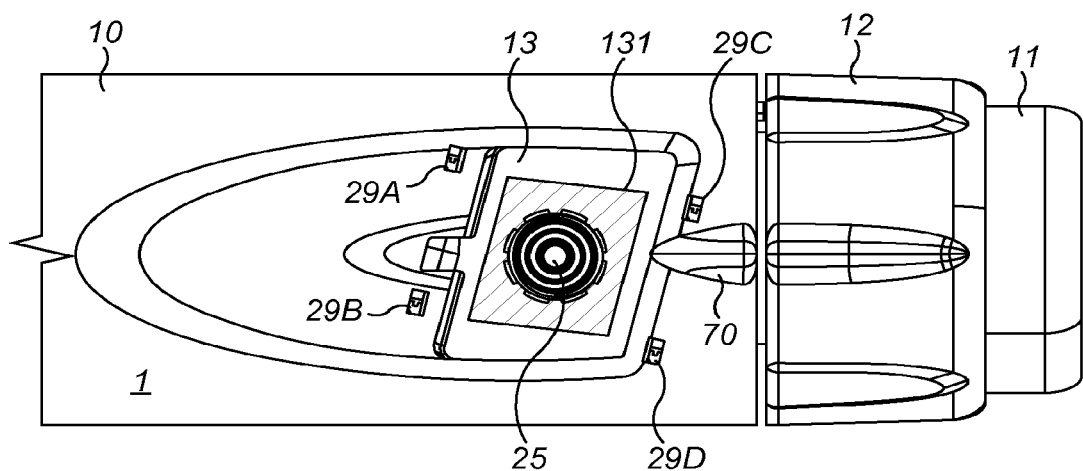
FIG. 15: a plan view which illustrates a location of a camera with respect to an injection device when a supplemental device according to an aspect of the present disclosure is attached to the injection device.
Figure 16:
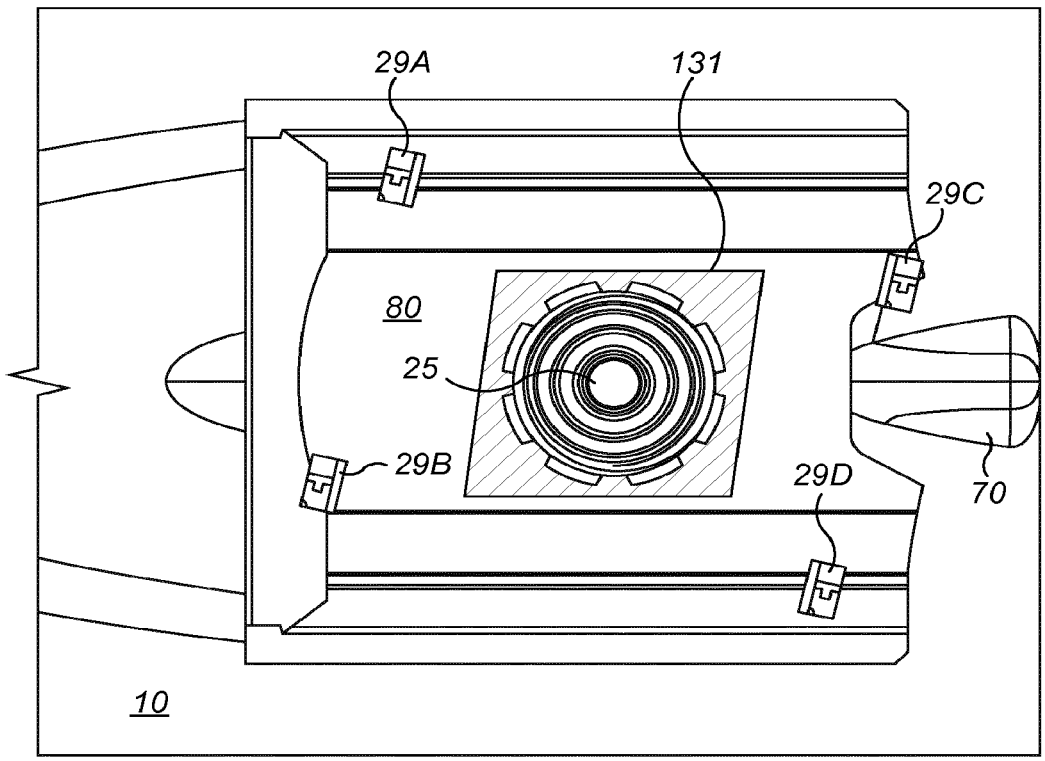
FIG. 16: a view similar to FIG. 15 and including a protection window.

As can be best seen from FIGS. 15 and 16, the optical arrangement comprising the camera 25 and the first to fourth light sources (e.g. LEDs) 29a-29d are skewed with respect to the main axis of the injection device 1. The optical components are skewed to be aligned with the skewed number sleeve 19 and dosage window 13. In the case of a SoloStar injection device, the amount of skew is 13 degrees.

The first to fourth light sources 29a-29d are separated from a lens 25a of the camera 25. In this example, they are distributed around the lens 25a. The light sources 29a-29d are configured to illuminate the dosage sleeve 19, so that numbers on the dosage sleeve can be read by the camera 25. As can be seen best from FIG. 13, the light sources 29a-29d are angled or tilted towards the centre of the dosage window 13. This provides more effective illumination of the dosage sleeve 19 and can improve overall efficiency of the illumination. In other embodiments, the light sources are not tilted and instead all radiate in a common direction from the plane in which they lie.

Figure 14:
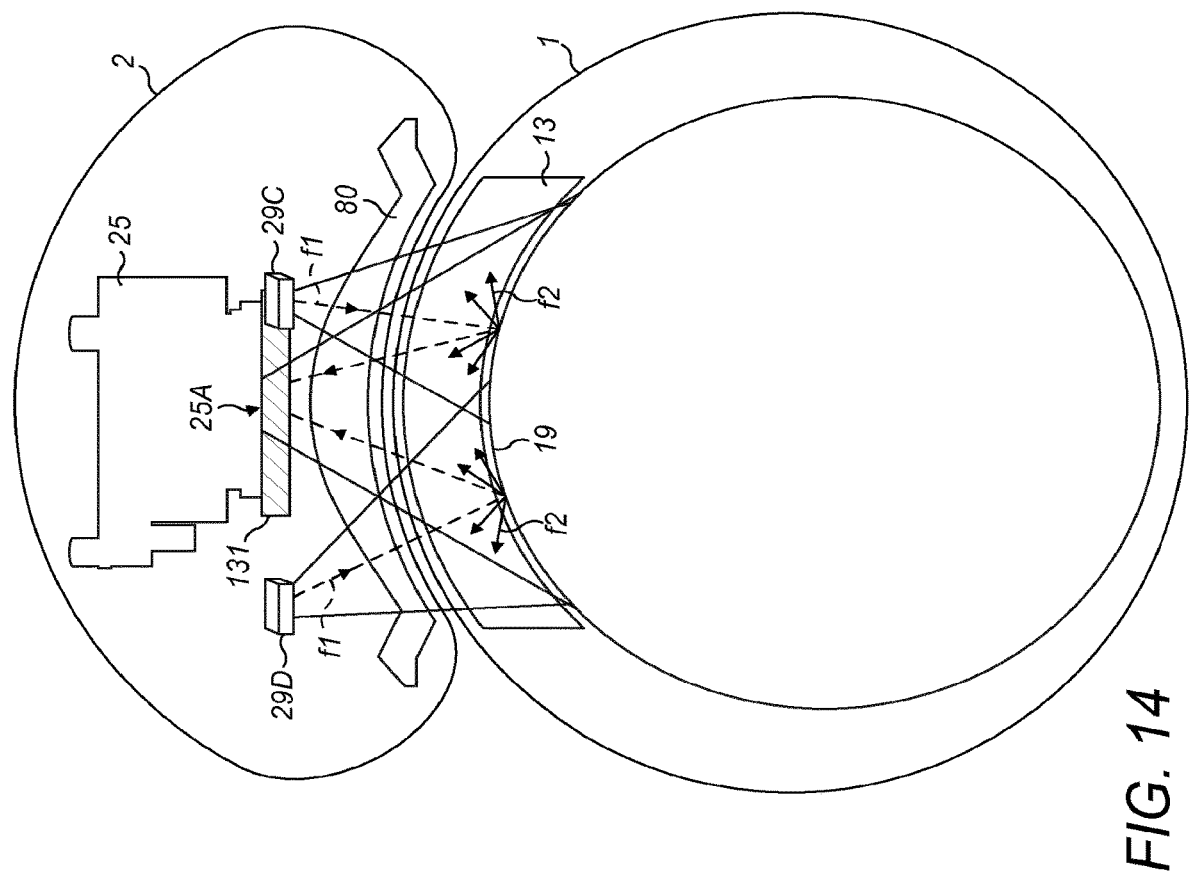
FIG. 14: a schematic drawing of an optical system according to an aspect of the present disclosure.

The optical system is perhaps best understood from FIG. 14, a highly schematic cross-sectional view that corresponds closely with FIG. 13 although it is the reverse view, i.e. it is taken from the opposite direction such that right in FIG. 13 is left in FIG. 14.

Although highly schematic, FIG. 14 shows illumination patterns of the third and fourth light sources 29d and 29c as being bordered by solid lines. These are merely schematic. In fact, the actual illumination of the dosage sleeve 19 is different because of refraction provided by the protection window 80 and the dosage window 13. In FIG. 14, the thickness of the dosage window 13 is exaggerated in order to aid explanation.

FIG. 14 shows that the field of view of the camera 25 converges at the camera lens 25a. It will be seen that the field of view of the camera 25 covers substantially the whole width of the dosage sleeve 19. Although not visible from FIG. 14, the field of view of the camera 25 also covers a sufficient part of the length of the dosage sleeve 19 that numbers provided on the dosage sleeve are captured by the camera 25 during operation.

The light sources 29a-29d are arranged so as to achieve substantially uniform illumination of the dosage sleeve 19. This is achieved by using light sources (e.g. LEDs) 29a-29d with substantially uniform illumination patterns within defined angular and spatial ranges. The light sources 29a-29d are positioned so that, taking into account the optical effects of the protection window 80 and the dosage window 13, a uniform illumination pattern is obtained at the dosage sleeve 19.

The light sources 29a-29d and the protection window 80 are arranged such that light paths meet boundaries between air and optical components at angles that are less than the angle of total internal reflection for the boundary. The protection window 80 is formed of a material that reflects relatively little light that is incident at angles less than the angle of total internal reflection.

With further reference to FIGS. 15 and 16, the first to fourth light sources 29a-29d are separated from the aforementioned filter 131. In other words they are offset relative to the filter 131 such that there can exist an optical path between the light sources 29a-29d and the dosage sleeve 19 in use, when the supplemental device 2 is coupled to the injection device 1. In this example, the light sources 29a-29d are distributed around the filter 131.

As already explained, FIG. 14 schematically illustrates a cross section through a supplemental device 2 coupled to an injection device 1. Functionality of this arrangement in use is as follows. The light sources 29a to 29d are controllable by the processor 24 to optically illuminate the dosage sleeve 19 with light of a first frequency $f_1$. This causes material defining a number on the dosage sleeve 19 to fluoresce. In other words by illuminating this material with light of a first frequency $f_1$, the material absorbs at least some of this light and then emits light of a second, different, frequency $f_2$. Light of the second frequency $f_2$ is emitted towards the filter 131 located in the field of view of the camera 25. The filter 131 is substantially transparent to light of the second frequency $f_2$ and so light of the second frequency $f_2$ passes through the filter 131 and is detected by the camera 25. In other words, fluorescence emitted from the dosage sleeve 19 passes through the filter 113 and is detected by the camera 25. However, any light of the first frequency $f_1$ which is reflected towards the camera 25 is not detected thereby because the filter 131 is configured to block light of the first frequency $f_1$. Light of the first frequency $f_1$ may be reflected towards the camera 25 for instance by the upper surface or the lower surface of the protection window 80 or the dosage window 13 in FIG. 14 (in other words, one of the window-air boundaries).

For exemplary purposes, FIG. 14 shows some light from the light sources 29a-29d passing through the protection window 80 and also the dosage window 13. This light becomes incident on material defining a number provided on the dosage sleeve 19 and causes this material to fluoresce. Some of the light from the light sources 29a-29d however is shown to reflect from the lower surface of the dosage window 13 towards the camera 25. Although, as mentioned above, this light is blocked from reaching the camera 25 by the filter 131.

The filter 131 in FIG. 14 is shown to occupy the whole of a cross section of the field of view of the camera 25, and thus occupies the whole of a cross section of an optical path between the dosage sleeve 19 and the camera 25. The camera 25 thus generates camera output on the basis of optical fluorescence emitted from the dosage sleeve 19 since only this light passes through the filter 131 in use. Fluorescence is only emitted by material on the dosage sleeve 19 that defines numbers. As a result, the camera output will be indicative of one or more numbers appearing on the dosage sleeve 19 in the field of view of the camera 25.

Camera output comprising images generated by the camera 25 in FIG. 14 can thus be processed in the manner heretofore described in order to determine what information is displayed on the dosage sleeve 19. For example camera output generated by the camera 25 on the basis of detected fluorescence may comprise an image in the same context as that in step 901 or 903 (see FIG. 4b). Therefore OCR can be performed on this image to determine a selected dose, as in step 904.

Various aspects of the optical system schematically illustrated in FIG. 14 will now be discussed more generally.

In a broad sense, the light sources 29a-29d are configured to generate optical illumination of a first frequency $f_1$ (or a narrow band of optical frequencies encompassing the first frequency $f_1$). Optical illumination, otherwise referred to as light, comprises electromagnetic radiation of a wavelength in the ultra violet, visible or infrared part of the electromagnetic spectrum. Ultraviolet light has a wavelength between approximately 10 nm and 400 nm for instance, visible light has a wavelength between approximately 400 nm and 750 nm for instance, and infrared light has a wavelength between approximately 750 nm and 1 mm for instance.

The light sources 29a-29d may thus be configured to generate at least one frequency of ultraviolet radiation. Optionally the light sources 29-29d may comprise ultraviolet LEDs.

An optical arrangement that comprises ultraviolet LEDs 29a-29d may be used to illuminate a dosage sleeve 19 that fluoresces visible light when illuminated with UV light. The material defining numbers on such a dosage sleeve 19 may be configured to absorb UV light of at least one frequency $f_1$ and thereby emit visible light of at least one frequency $f_2$. Such material may comprise an FG series UV fluorescent pigment for example UVPN non-soluble white powder, which fluoresces white/blue when exposed to long wave UV (365 nm-400 nm) or UVSWR/G non-soluable powder which fluoresces red/green when exposed to short wave UV (254 nm) (see https://www.maxmax.com/aUVInvisiblePowders.asp). The filter 131 in this embodiment is configured to substantially block the passage of UV light (or at least to substantially block the passage of the or each frequency of UV light emitted by the ultraviolet LEDs 29a-29d). The filter 131 is further configured to be substantially transparent to visible light (or at least to be substantially transparent to the or each frequency of visible light emitted as fluorescence from the dosage sleeve 19).

Broadly speaking the optical system causes optical fluorescence to be generated by an injection device 1 upon illumination thereof (specifically upon illumination of an area of the dosage sleeve 19) with light of at least one frequency. The material used to generate the fluorescence (specifically, the material which defines numbers provided on the dosage sleeve 19) should be configured to generate fluorescence having a frequency $f_2$ different to light emitted by the light sources 29a-129d having a frequency $f_1$.

In view of the foregoing, the light sources 29a-29d may be configured to generate one of ultraviolet radiation, visible radiation and infrared radiation. The material provided on the dosage sleeve 19 that is used to generate fluorescence may thus be configured to generate fluorescence that comprises another of ultraviolet radiation, visible radiation and infrared radiation.

Alternatively, the material provided on the dosage sleeve 19, that is used to generate fluorescence, may be configured to generate fluorescence of the same kind of light as that emitted from the light sources, albeit of a different frequency. For instance the light sources 29a-29d may be configured to generate ultraviolet radiation, and the fluorescence capable of being generated by the material provided on the dosage sleeve 19 may also be ultraviolet radiation, albeit of a different frequency.

Reference is again made to FIG. 14 for the purpose of outlining specific details of an injection device 1 that is capable of being used in conjunction with a supplemental device 2 of the kind described herein.

Such an injection device may be substantially of the kind heretofore described and may comprise, for instance, a Sanofi Solostar insulin injection device. However an injection device 1 capable of being used in conjunction with a supplemental device 2 of the kind in FIG. 14 is configured such that numbers provided on the dosage sleeve 19 are defined by material which optically fluoresces when illuminated with one or more frequencies of optical radiation. In other words, this material emits light having a frequency $f_2$ when illuminated with light of another frequency $f_1$.

Numbers provided on the dosage sleeve 19 are capable of being viewed through a protection window 13 of the injection device 1 (see FIGS. 1a and 14). These numbers are indicative of a selected dose to be injected, or in other words, a dialled amount of dose. In the case of an injection device configured similarly to that shown in FIGS. 1a and 1b, turning the dosage knob 12 will cause the dosage sleeve 19 to rotate helically within the injection device 1. This enables a particular number that corresponds to a dialled quantity of dose to be moved into alignment with the dosage window 13.

The material which defines numbers on the dosage sleeve 19 may comprise a pigment and it is the pigment that is capable of generating fluorescence. For example numbers on the dosage sleeve 19 may be provided, printed, drawn or applied thereon using material having a different colour to that of the surface on which they are located. In one example the dosage sleeve 19 may be white and the numbers provided thereon may be black. Notwithstanding the colour of the numbers, the material defining such numbers may be capable of fluorescing when illuminated with light of one or more particular frequencies. This material may comprise a pigment, or have such a pigment dispersed within it, and it is the pigment that is capable of generating the fluorescence.

Various alterations and modifications to the embodiments described above will now be discussed.

For instance, instead of the material on the dosage sleeve 19 that defines numbers being able to fluoresce, this material may not be configured to do so. Instead the surface of the dosage sleeve 19 surrounding the numbers defined by this material may be configured to generate fluorescence. In this embodiment OCR recognition could still be performed to determine what number is in the field of view of the camera 25. This is because numbers will be recognisable from the shape of the dark section(s) in images generated by the camera 25. For instance, if the surface surrounding a number provided on the dosage sleeve 19 is caused to fluoresce, the dark area that does not fluoresce will be apparent. The shape of the dark area is indicative of the number provided on the dosage sleeve and is capable of being detected and analysed using OCR to determine what number the shape of the dark area corresponds to.

Although embodiments have been described in the context of an injection device, aspects of the present disclosure are applicable to devices other than injection devices. For instance, injection devices 1 of the kind described herein could be modified so as to merely comprise liquid dispensing devices, or in other words devices that eject liquid but are not used to inject it. This may be achieved by a simple modification of the needle 15 to a nozzle type feature (see FIG. 1a). Therefore, supplemental devices 2 of the kind described herein can be used with liquid dispensing devices other than injection devices.

In some embodiments the filter 131 may be configured to allow light having a frequency within a narrow band of optical frequencies centred on the second frequency $f_2$ mentioned above to pass through it (i.e. the second frequency $f_2$ being that of optical fluorescence emitted from the dosage sleeve 19). Also, in some embodiments the filter 131 may be configured to block light having a frequency within a narrow band of optical frequencies centred on the first frequency $f_1$ mentioned above (i.e. the first frequency $f_1$ being that of light emitted by the or each light source 29a-29d).

Information has been described as being provided on a dosage sleeve 19 in the form of one or more numbers. Also, this information has been described as being identified via the use of OCR. However, more generally, information provided on the dosage sleeve 19 could instead or additionally comprise one or more signs, symbols, letters or code segments. Instead of OCR, pattern recognition functionality could be used in a more general sense to identify signs, symbols, letters or parts of a code that are viewable through a dosage window 13. Such information could then be used to determine a selected (or dialled) dose amount. For instance a particular sign, symbol, letter or code segment could be associated with an amount of selected (dialled) dose. A table associating such signs, symbols, letters or code segments with quantities of dose selected might be stored in the main memory 241 or the supplementary memory 243 (see FIG. 3) and be accessible to the processor 24.

Various other alternatives to the subject matter described herein will be apparent to the skilled person and all such alternatives are within the scope of the disclosure unless excluded by the scope of the claims.

For instance, instead of LEDs, any other suitable light sources may be used. Suitable light sources may include light bulbs, laser diodes and organic LEDs.

Although four light sources are included in the shown embodiments (e.g. illumination sources 29a-29d), in other embodiments there are one, two, three, five or more than five light sources. The choice of the number of light sources may depend on the particular light source type chosen, brightness, efficiency and cost requirements. Four light sources provides sufficient illumination of a dosage sleeve in most instances whilst having relatively little hardware.

Although the protection window 80 is described as being located close to the dosage window 13 when the supplemental device 2 is in position on an injection device 1 in the embodiments above, they may instead be separated by a significant distance. Providing the protection window 80 close to the dosage window 13 contributes to providing a compact arrangement.

Figure 17:
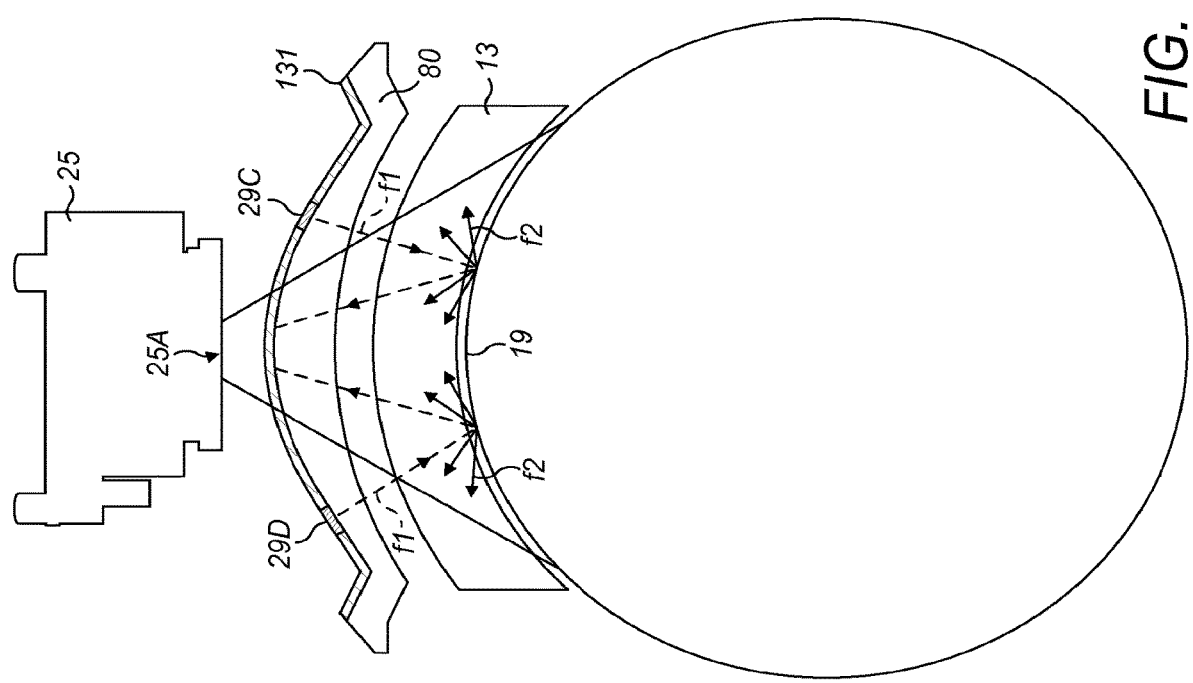
FIG. 17: a schematic drawing of an optical system according to another aspect of the present disclosure.

The filter 131 may be coupled to the protection window 80. FIG. 17 illustrates one such arrangement, wherein the light sources 29a to 29d emit light directly into, and thus through, the protection window 80 through gaps in the filter 131 (or portions thereof that are transparent to at least one frequency of light from the light sources 29a to 29d). It will be appreciated that in this arrangement, illustrated in FIG. 17, the optical path between the dosage sleeve 19 and the camera 25 does not include the space extending between these two components in which the illumination sources 29a-29d are located. This is because light reflected towards the illumination sources cannot travel through the illumination sources. In other words the optical path between the dosage sleeve 19 and the camera 25 in FIG. 17 includes any line between these two components that is not blocked by an illumination source 29a-29d.

Figure 19:
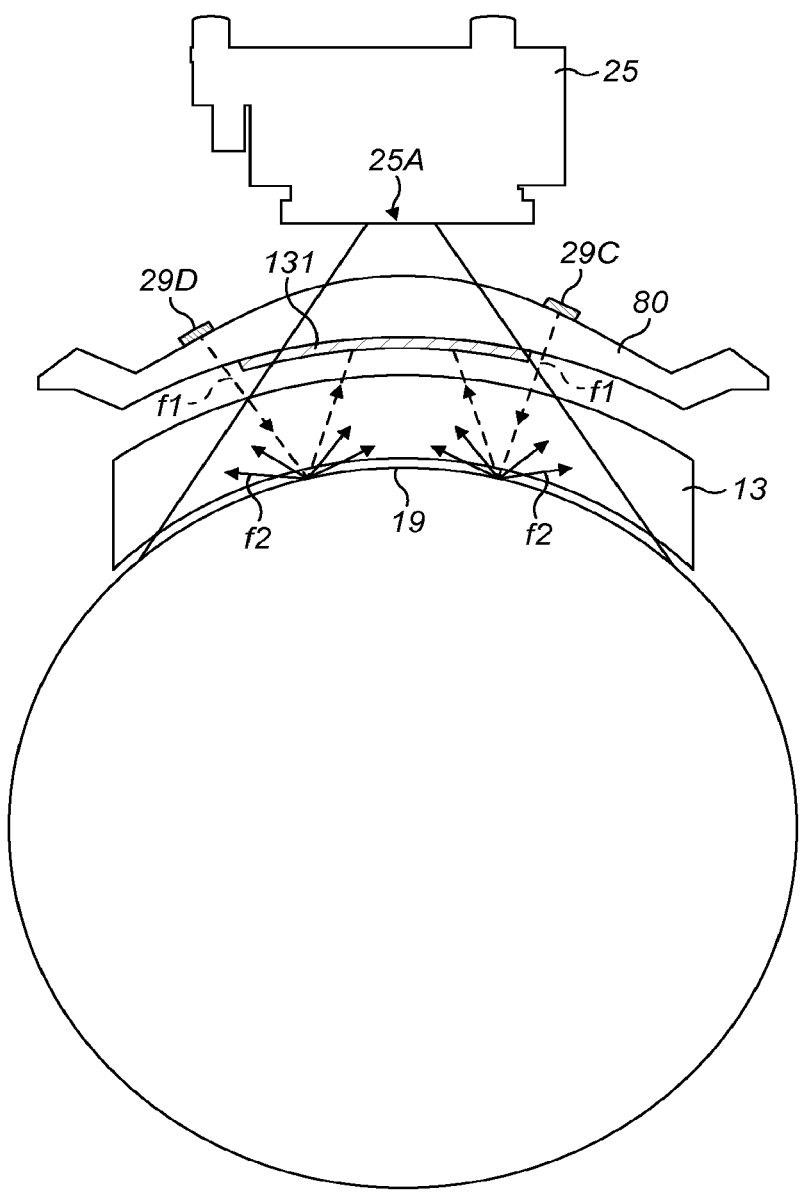
FIG. 19: a schematic drawing of an optical system according to another aspect of the present disclosure.

Although the filter 131 is coupled to the upper side of the protection window 80 in FIG. 17, the filter 131 could instead be coupled to the lower side of the protection window 80 as in FIG. 19. The illumination sources 29a to 29d need to be in a position in which at least one frequency of light emitted therefrom can be directed onto the dosage sleeve 19. The filter 131 should be located across the entire cross section of the line of sight of the camera 25, which is illustrated by the solid lines extending from the camera 25 in FIG. 19. Furthermore, the filter 131 in this arrangement (at least the part thereof facing the camera 25 in FIG. 19) should be configured to absorb light of the or each frequency emitted by the illumination source(s). The optical path between the dosage sleeve 19 and the camera 25 in this arrangement is any line extending between these two components that is within the line of sight of the camera 25, illustrated by the solid lines extending from the camera 25 in FIG. 19.

Figure 18:
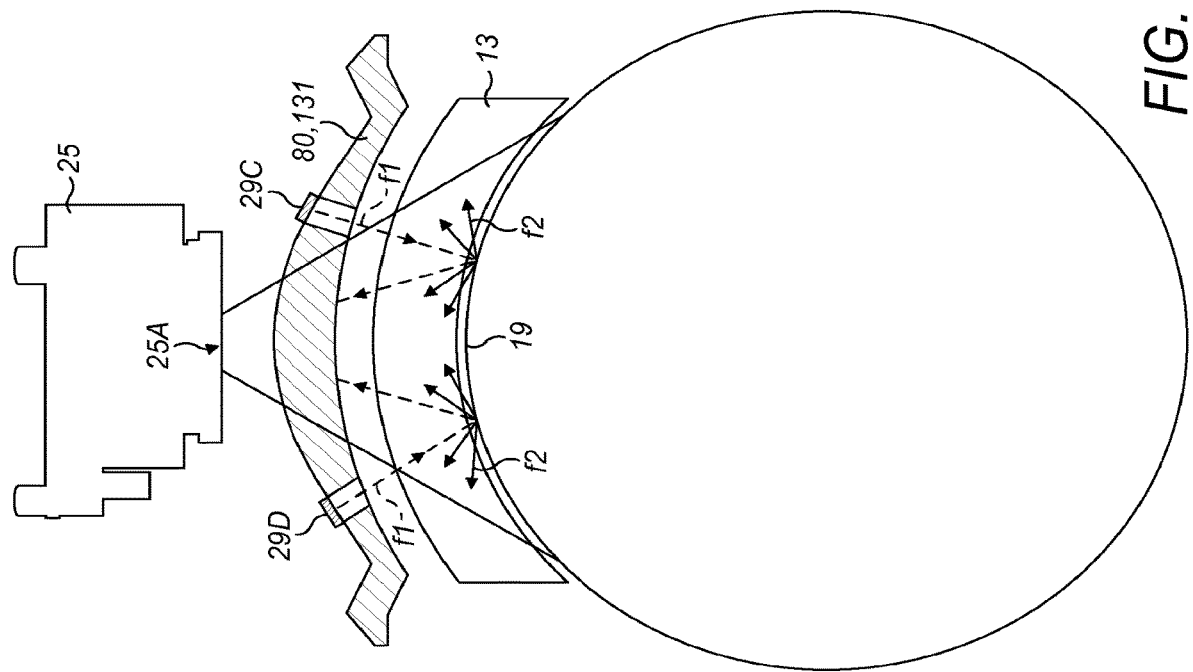
FIG. 18: a schematic drawing of an optical system according to a further aspect of the present disclosure.

In other embodiments the filter 131 may be embedded in or comprise an integral part of the protection window 80, and may comprise for instance a tinted part of the protection window 80. FIG. 18 illustrates one such arrangement, wherein the light sources 29a to 29d emit light directly into, and thus through, parts of the protection window 80 through gaps in the filter 131. Another way of thinking of such an arrangement would be to describe it as a filter 131 with transparent portions in it that are configured to perform the function of the window 80. In the case that the filter 131 comprises an integral part of the protection window 80 a separate filter 131 may not be provided. It is further envisaged that the transparent window-like portions may comprise part of the respective illumination sources 29a-29d themselves, in which case a separate window 80 (or window portion) is not provided. It will be appreciated that in the arrangements mentioned in this paragraph, for instance that illustrated in FIG. 18, the optical path between the dosage sleeve 19 and the camera 25 does not include the space extending between these two components in which the illumination sources 29a-29d are located. This is because light reflected towards the illumination sources cannot travel through the illumination sources. In other words the optical path between the dosage sleeve 19 and the camera 25 in FIG. 18 includes any line between these two components that is not blocked by an illumination source 29a-29d.

The filter 131 may be configured to either reflect or absorb light of the or each frequency emitted by the light sources 29a-29d.

In some embodiments the supplemental device 2 may be configured such that, in use, an optical path does not extend directly between the dosage sleeve 19 and the camera 25. For instance light may be reflected from the dosage sleeve 19, through the dosage window 13 and protection window 80, and then redirected by one or more reflective surfaces (e.g. a mirror) onto the camera 25. In such embodiments an optical path does not extend directly between the dosage sleeve 19 and the camera 25. Instead the optical path extends indirectly between the dosage sleeve 19 and the camera 25 via the one or more reflective surfaces (e.g. mirrors). Nevertheless the filter 131 is located on this optical path and occupies the whole of the cross sectional width thereof. The filter 131 thus restricts light of one or more frequencies being directed along this optical path onto the camera 25.

With reference to FIG. 14, the material defining the numbers on the dosage sleeve 19 may fluoresce infra-red light when illuminated with visible light. In such an embodiment the material defining numbers on such a dosage sleeve 19 comprise IRDC2—IR fluorescent powder available for purchase at www.maxmax.com. IRDC2 fluoresces at both 880 nm and 1050 nm when stimulated with a 450 nm and 630 nm light source. The filter 131 in this embodiment is configured to substantially block the passage of visible light (or at least to substantially block the passage of the or each frequency of visible light emitted by the LEDs 29a-29d in order to stimulate fluorescence). The filter 131 is further configured to be substantially transparent to infrared light (or at least to be substantially transparent to the or each frequency of infrared light emitted as fluorescence from the dosage sleeve 19).

Although supplemental device embodiments have been described as being provided with a protection window 80, such a protection window 80 is not strictly necessary although the absence of such a protection window increases the likelihood of dirt ingress into the supplemental device 2.

The invention claimed is:
1. An injection device comprising:
a sleeve comprising one or more markings indicating a dose of medicament; and
a window through which a part of the sleeve and the one or more markings are visible, the injection device being configured to change the part of the sleeve that is visible through the window as the dose of medicament is dispensed,
wherein the one or more markings are formed of a fluorescent material that emits fluorescence when illuminated with an external light source of a particular frequency,
wherein the fluorescent material is configured such that when illuminated with visible radiation, the fluorescent material emits through the window optical fluorescence that is infrared radiation.

2. The injection device of claim 1, wherein the fluorescent material is in a shape of information that indicates the dose of medicament.

3. The injection device of claim 1, wherein the fluorescent material outlines a shape of information that indicates the dose of medicament.

4. The injection device of claim 1, further comprising a container containing the medicament, the medicament comprising a pharmaceutically active compound.

5. The injection device of claim 1, wherein the one or more markings are configured to have a different color to that of a surface of the sleeve on which the one or more markings are located.

6. The injection device of claim 1, wherein the one or more markings define one or more numbers.

7. The injection device of claim 1, wherein the one or more markings comprise one or more signs, symbols, letters or code segments.

8. The injection device of claim 1, wherein the fluorescent material comprises a pigment that is capable of generating fluorescence.

9. The injection device of claim 8, wherein the pigment comprises a fluorescent powder.

10. The injection device of claim 1, wherein the visible radiation from the external light source comprises both a 450 nm wavelength and a 630 nm wavelength of visible radiation.

11. The injection device of claim 10, wherein the infrared radiation comprises both a 800 nm wavelength and a 1050 nm wavelength of infrared radiation when the fluorescent material is illuminated with the 450 nm wavelength of infrared radiation and the 630 nm wavelength of visible radiation.

12. The injection device of claim 1, wherein the sleeve is configured to rotate helically within the injection device to cause the one or more markings to become visible in the window.

13. The injection device of claim 1, wherein the window is inclined with respect to an axis of the injection device such that the one or more markings becoming visible in a helical fashion.

14. A method comprising:
illuminating a surface of a sleeve accommodated inside a housing of an injection device, the surface comprising one or more markings formed of a fluorescent material;
detecting radiation emitted from the fluorescent material; and
determining a dose of a medicament based on the detected radiation,
wherein a part of the sleeve and the one or more markings are visible through a window provided in the housing of the injection device,
wherein illuminating the surface comprises emitting, by a light source, visible radiation, and
wherein the radiation emitted from the fluorescent material is infrared radiation.

15. The method of claim 14, wherein the radiation emitted from the fluorescent material is detected by a camera.

16. The method of claim 14, further comprising filtering the radiation emitted from the fluorescent material prior to detecting the radiation emitted from the fluorescent material.

17. The method of claim 14, wherein emitting the visible radiation comprises emitting both a 450 nm wavelength of visible radiation and a 630 nm wavelength of visible radiation.

18. The method of claim 17, wherein emitting the infrared radiation comprises emitting both a 800 nm wavelength of infrared radiation and a 1050 nm wavelength of infrared radiation when the fluorescent material is illuminated with the 450 nm wavelength of infrared radiation and the 630 nm wavelength of visible radiation.

19. The method of claim 14, wherein the sleeve is configured to rotate helically within the injection device to cause the one or more markings to become visible in the window.

20. The method of claim 14, wherein the window is inclined with respect to an axis of the injection device such that the one or more markings becoming visible in a helical fashion.

* * * * *